United States Patent [19]

Moore et al.

[11] Patent Number: 4,652,556

[45] Date of Patent: Mar. 24, 1987

[54] FUNGICIDAL N-CYANOALKYL-N-HALOALKYLTHIO SULFONAMIDES

[75] Inventors: Joseph E. Moore, Richmond; Yuh-Lin Yang, Hercules; Robert K. Griffith, Corte Madera; David C. K. Chan, Petaluma, all of Calif.

[73] Assignee: Chevron Research Company, San Francisco, Calif.

[21] Appl. No.: 767,009

[22] Filed: Aug. 19, 1985

Related U.S. Application Data

[63] Continuation-in-part of Ser. No. 730,230, May 3, 1985, abandoned, which is a continuation of Ser. No. 653,734, Sep. 20, 1984, abandoned.

[51] Int. Cl.$^4$ .................. A01N 41/06; C07C 143/72
[52] U.S. Cl. ........................... 514/155; 260/397.7 R; 514/438; 514/523; 514/526; 549/75; 558/303; 558/390; 558/408; 558/426; 558/430; 558/431; 558/432; 558/433; 558/434; 558/437
[58] Field of Search ............ 260/465 D, 465 E, 465.4, 260/465.5 R, 464, 397.7 R; 549/75; 514/155, 438, 523, 526, 562; 558/303, 390, 408, 426, 430, 431, 432, 433, 434, 437

[56] References Cited

U.S. PATENT DOCUMENTS

| | | | |
|---|---|---|---|
| 3,178,447 | 4/1965 | Kohn | 260/453 RW |
| 4,283,416 | 8/1981 | Chan | 514/601 |
| 4,350,831 | 9/1982 | Chan et al. | 564/80 |
| 4,402,980 | 9/1983 | Kühle et al. | 514/601 |
| 4,511,735 | 4/1985 | Magee | 514/601 |

Primary Examiner—Dolph H. Torrence
Attorney, Agent, or Firm—S. R. LaPaglia; T. G. DeJonghe; S. L. Biggs

[57] ABSTRACT

Compounds of the formula:

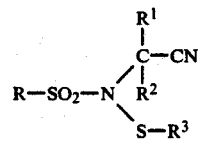

wherein R is aryl of 6 to 12 carbon atoms or aralkyl of 7 to 14 carbon atoms either optionally substituted with 1 to 3 substituents independently selected from lower alkyl of 1 to 6 carbon atoms, lower alkoxy of 1 to 6 carbon atoms, lower alkylthio of 1 to 6 carbon atoms, lower alkylsulfinyl of 1 to 6 carbon atoms, lower alkylsulfonyl of 1 to 6 carbon atoms, halogen, trihalomethyl, nitro, cyano or carboxyl; alkyl of 1 to 10 carbon atoms, cycloalkyl of 3 to 10 carbon atoms, lower alkenyl of 2 to 6 carbon atoms, or lower alkynyl of 2 to 6 carbon atoms, all optionally substituted with 1 to 3 halogen atoms; lower alkoxyalkylene; lower alkylene carbalkoxy; lower alkylthioalkylene; lower alkylsulfinylalkylene; or lower alkylsulfonylalkylene; $R^1$ and $R^2$ are independently hydrogen, lower alkyl of 1 to 6 carbon atoms, aryl of 6 to 12 carbon atoms, or thienyl, or taken together form an alkylene bridge to give a cycloalkyl group of 3 to 10 carbon atoms; and $R^3$ is alkyl of 1 to 3 carbon atoms substituted with 3 to 6 halogen atoms or trihalovinyl are fungicidal.

85 Claims, No Drawings

FUNGICIDAL N-CYANOALKYL-N-HALOALKYLTHIO SULFONAMIDES

This application is a continuation-in-part of application U.S. Ser. No. 730,230, filed May 3, 1985, abandoned. which is a continuation of application U.S. Ser. No. 653,734, filed Sept. 20, 1984, now abandoned.

BACKGROUND OF THE INVENTION

The present invention relates to novel N-cyano-alkyl-N-haloalkylthio sulfonamides which are fungicidal. The compounds of this invention are useful in protecting plants against a variety of fungal pests.

Certain N-polyhaloalkylthio compounds have been disclosed as fungicidal. See, e.g., commonly-assigned U.S. Pat. No. 3,178,447 and U.S. Pat. No. 4,511,735.

In addition, certain N-tetrachloroethylthio substituted sulfonamides have been disclosed as effective in killing mites and mite eggs. See, e.g., commonly-assigned U.S. Pat. No. 4,350,831.

U.S. Pat. No. 4,402,980 discloses N-sulphenylated sulphonic acid cycloalkylamides of the formula

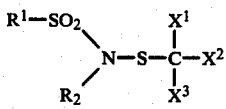

wherein
$R^1$ denotes lower alkyl, chloroalkyl or dialkylamino,
$R^2$ denotes a cycloalkyl radical which is optionally substituted by lower alkyl, and
$X^1$, $X^2$ and $X^3$ are identical or different and represent fluorine or chlorine,
and their use as microbiocides.

SUMMARY OF THE INVENTION

The novel N-cyanoalkyl-N-haloalkylthio sulfonamide compounds of the present invention may be represented by the general formula:

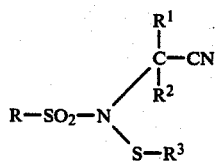
(I)

wherein R is aryl of 6 to 12 carbon atoms or aralkyl of 7 to 14 carbon atoms either optionally substituted with 1 to 3 substituents independently selected from lower alkyl of 1 to 6 carbon atoms, lower alkoxy of 1 to 6 carbon atoms, lower alkylthio of 1 to 6 carbon atoms, lower alkylsulfinyl of 1 to 6 carbon atoms, lower alkylsulfonyl of 1 to 6 carbon atoms, halogen, trihalomethyl, nitro, cyano or carboxyl; alkyl of 1 to 10 carbon atoms, cycloalkyl of 3 to 10 carbon atoms, lower alkenyl of 2 to 6 carbon atoms, or lower alkynyl of 2 to 6 carbon atoms, all optionally substituted with 1 to 3 halogen atoms; lower alkoxyalkylene; lower alkylene carbalkoxy; lower alkylthioalkylene; lower alkylsulfinylalkylene; or lower alkylsulfonylalkylene; $R^1$ and $R^2$ are independently hydrogen, lower alkyl of 1 to 6 carbon atoms, aryl of 6 to 12 carbon atoms, or thienyl, or taken together form an alkylene bridge to give a cycloalkyl group of 3 to 10 carbon atoms; and $R^3$ is alkyl of 1 to 3 carbon atoms substituted with 3 to 6 halogen atoms or trihalovinyl.

Among other factors, the present invention is based on our finding that these compounds are surprisingly effective in controlling fungi, in particular, controlling certain plant fungal diseases.

In addition, some of these compounds are acaricidal being particularly active as mite ovicides, especially those compounds where $R^3$ is 1,1,2,2-tetrachloroethyl.

Preferred compounds include those where R is lower alkyl or lower alkenyl.

Preferred R groups include methyl, ethyl, n-propyl, isopropyl, n-butyl and vinyl.

Especially preferred are compounds where R is methyl.

Preferred $R^1$ and $R^2$ groups include hydrogen, methyl, ethyl and thienyl or those where $R^1$ and $R^2$ are taken together form a cyclopentyl or cyclohexyl group.

Preferred $R^3$ groups include 1,1,2,2-tetrahaloethyl, trihalomethyl, and trihalovinyl. Examples include 1,1,2,2-tetrachloroethyl, 2-fluoro-1,1,2,2-tetrachloroethyl, trichloromethyl, dichlorofluoromethyl and the like. Particularly preferred are compounds where $R^3$ is 1,1,2,2-tetrachloroethyl.

The especially preferred halogen is chlorine.

Particularly preferred compounds include those where R is lower alkyl, $R^1$ and $R^2$ are independently methyl or ethyl and $R^3$ is 1,1,2,2-tetrachloroethyl.

DEFINITIONS

As used herein, the following terms have the following meanings unless expressly stated to the contrary.

The term "alkyl" refers to both straight- and branched-chain alkyl groups. The term "lower alkyl" refers to both straight- and branched-chain alkyl groups having a total of from 1 to 6 carbon atoms and includes primary, secondary and tertiary alkyl groups. Typical lower alkyls include, for example, methyl, ethyl, n-propyl, isopropyl, n-butyl, isobutyl, t-butyl, n-pentyl, n-hexyl, and the like.

The term "cycloalkyl" refers to cyclic alkyl groups. The term "lower cycloalkyl" refers to groups having from 3 to 6 carbon atoms in the ring, and includes cyclopropyl, cyclobutyl, cyclopentyl, and cyclohexyl.

The term "alkylene" refers to straight- and branched-chain alkylene groups and includes groups of the formula $-(CH_2)_m-$ wherein m is an integer greater than zero, as well as groups such as 2-methylpropylene (e.g.,

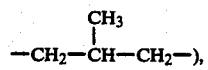

3-methylpentylene (e.g.,

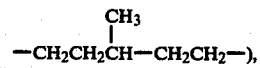

and the like. Thus, typical alkylene groups include, methylene, ethylene, propylene, 2-methylbutylene, and the like.

The term "alkylthio" refers to the group R'S— wherein R' is alkyl. The term "lower alkylthio" refers to alkylthio groups having 1 to 6 carbon atoms; examples include methylthio, ethylthio, n-hexylthio, and the like.

The term "alkylsulfinyl" refers to the group

wherein R' is alkyl. The term "lower alkylsulfinyl" refers to alkylsulfinyl groups having 1 to 6 carbon atoms; and includes, for example, methylsulfinyl, ethylsulfinyl, n-pentylsulfinyl, and the like.

The term "alkylsulfonyl" refers to the group

wherein R' is alkyl. The term "lower alkylsulfonyl" refers to alkylsulfonyl groups having from 1 to 6 carbon atoms; examples include methylsulfonyl, ethylsulfonyl, n-propylsulfonyl, and the like.

The term "alkoxy" refers to the group —OR' wherein R' is an alkyl group. The term "lower alkoxy" refers to alkoxy groups having from 1 to 6 carbon atoms; examples include methoxy, ethoxy, n-hexoxy, n-propoxy, isopropoxy, isobutoxy, and the like.

The term "alkenyl" refers to unsaturated alkyl groups having a double bond [e.g., $CH_3CH=CH(CH_2)_2-$] and includes both straight- and branched-chain alkenyl groups. "Lower alkenyl" refers to groups having a total of from 2 to 6 carbon atoms. Typical lower alkenyl groups include, for example, vinyl, propenyl, but-3-enyl, hex-4-enyl, 2-methyl-pent-4-enyl, and the like.

The term "halo" or "halogen" refers to the groups fluoro, chloro, bromo and iodo.

The term "haloalkenyl" refers to alkenyl groups substituted with from 1 to 3 halogen atoms. "Lower haloalkyl" refers to groups having a total of from 2 to 6 carbon atoms, and includes, for example, 1-chloro-propenyl, 2,3-dibromo-but-3-enyl, and the like.

The term "alkynyl" refers to unsaturated alkyl groups having a triple bond (e.g., $CH_3C\equiv CCH_2CH_2-$) and includes both straight- and branched-chain alkynyl groups. "Lower alkynyl" refers to groups having a total of from 2 to 6 carbon atoms. Typical lower alkynyl groups include propynyl, but-3-ynyl, hex-4-ynyl, 2-methyl-pent-4-ynyl, and the like.

The term "hydroxy alkyl" refers to the group —R'OH wherein R'' is branched or unbranched alkylene and the hydroxy can be on a primary, secondary or a tertiary carbon. Examples include hydroxyethyl and 2-hydroxy-propyl and 2-hydroxy-2-methylbutyl.

The term "aryl" refers to aryl groups having from 6 to 12 carbon atoms and includes, for example, phenyl, p-chlorophenyl, m-methylphenyl, p-butylphenyl, m-trifluoromethylphenyl, naphthyl, and the like.

The term "aralkyl" refers to an alkyl group of 1 to 4 carbons substituted with an aryl group of from 6 to 12 carbons and includes, for example, benzyl, p-chlorobenzyl, P-methylbenzyl and 2-phenylethyl.

The term "alkylamino" refers to the group R'R''N— wherein R' is alkyl and R'' is hydrogen or alkyl. The term "lower alkylamino" refers to alkylamino groups having 1 to 6 carbon atoms. Typical alkylamino groups include methylamino, ethylamino, diethylamino, dimethylamino, and the like.

The term "alkoxyalkylene" refers to groups having the formula R'OR''— wherein R' is alkyl and R'' is straight- or branched-chain alkylene. The term "lower alkoxyalkylene" refers to alkoxyalkylene groups where R' is lower alkyl and R'' has a chain length of up to 6 carbon atoms. Typical lower alkoxyalkylene groups include, for instance, methoxymethylene, methoxypropylene, isopropoxybutylene, hexoxyethylene, and the like.

The term "alkylene carbalkoxy" refers to the group

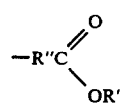

wherein R' is alkyl and R'' is alkylene. The term "lower alkylene carbalkoxy" refers to those groups where R' is lower alkyl and R'' has a chain length of up to 6 carbon atoms. Examples include carbethoxymethyl, carbomethoxyethyl, and the like.

The term "alkylthioalkylene" refers to groups having the formula R'SR''— wherein R' is alkyl and R'' is straight- or branched-chain alkylene. The term "lower alkylthioalkylene" refers to alkylthioalkylene groups wherein R' is lower alkyl and R'' has a chain length of up to 6 carbon atoms. Typical lower alkylthioalkylene groups include ethylthioethylene, isopropylthiobutylene, hexylthioethylene, and the like.

The term "alkylsulfinylalkylene" refers to groups having the formula

wherein R' is alkyl and R'' is straight- or branched-chain alkylene. The term "lower alkylsulfinylalkylene" refers to alkylsulfinylalkylene groups where R' is lower alkyl and R'' has a chain length of up to 6 carbon atoms. Typical examples include ethylsulfinylmethylene, methylsulfinylethylene, isopropylsulfinylbutylene, and the like.

The term "alkylsulfonylalkylene" refers to groups having the formula

wherein R' is alkyl and R'' is straight- or branched-chain alkylene. The term "lower alkylsulfonylalkylene" refers to those alkylenesulfonylalkylene groups where R' is lower alkyl and R'' has a chain length of up to 6 carbon atoms, and includes, for instance, methylsulfonylethylene, propylsulfonylmethylene, isopropylsulfonylbutylene, hexylsulfonylethylene, and the like.

Pests are any insect, rodent, nematode, fungus, weed, or any form of terrestrial or aquatic plant or animal life or virus, bacterial organism or other microorganism (except those viruses, bacteria or other microorganisms existing in living humans or other living animals) considered injurious to health, the environment or man's economic well-being.

DETAILED DESCRIPTION OF THE INVENTION

The compounds of the present invention may be conveniently prepared by following the following reaction scheme:

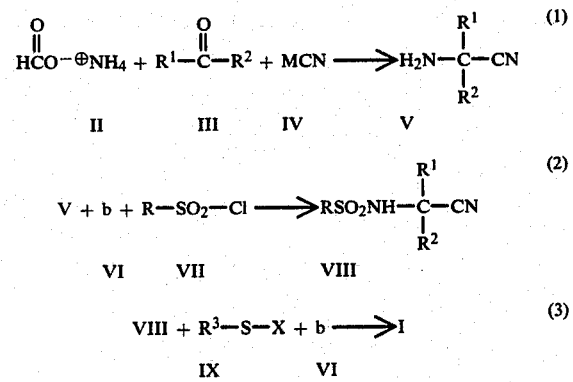

wherein R, $R^1$, $R^2$ and $R^3$ are as previously defined in conjunction with Formula I, X is a halogen, M is an alkali metal, and b is a base.

Reaction (1) involves addition of an amino and a cyano group to carbonyl-containing intermediate III. Various conventional ammonia sources (amination reagents) may be used. Suitable reagents include ammonium formate, ammonium acetate, ammonium carbonate, and ammonium chloride/ammonium hydroxide. Other conventional sources of ammonia may be used.

By way of illustration, ammonium formate is used as the ammonia source. Thus, reaction (1) is conducted by combining approximately equimolar amounts of II, III and IV in solvent. Although the reactants may be added in any order, it is preferred to add IV to a stirred solution of II and III in solvent. Reactant (II) may be prepared in situ from formic acid. Suitable solvents include water. The reaction is conducted at a temperature of about 0° C. to about 50° C., preferably from about 5° C. to about 30° C., and is generally complete within about 1 to about 4 hours. The product V is isolated by conventional procedures such as extraction, distillation, column chromatography and the like. Alternatively, V may be isolated as a salt, such as the hydrochloride, by precipitation.

Reaction (2) is conducted by combining approximately equimolar amounts of V, VI and VII in solvent. Although the reactants may be added in another order, it is preferred to add VII in solvent to a stirred mixture of V and VI in solvent. Suitable bases, b, include organic bases such as triethylamine, pyridine, 4-dimethylaminopyridine, and the like, or inorganic bases, such as sodium or potassium hydroxide. Suitable solvents include water, organic solvents, such as methylene chloride, chloroform, benzene or the like. The reaction is conducted at a temperature of about 0° C. to about 50° C., or, for convenience, at ambient temperature. The reaction is generally complete within about 2 hours. The product, VIII, is isolated by conventional procedures such as washing, stripping, filtration, crystallization, column chromatography and the like.

Reaction (3) is conducted by combining VIII, IX and VI in solvent. Although the reactants may be combined in another order, it is preferred to add VI in solvent to a stirred mixture of VIII and IX in solvent. Although approximately equimolar amounts of VI, VIII and IX may be used, it is preferred to use a slight excess of IX and VI in relation to VIII, on the order of about 1.05 to about 1.1 mole IX per mole VIII and about 1.1 to about 1.2 mole VI per mole VIII. Suitable bases, VI, include organic bases such as triethylamine, pyridine, and the like or inorganic bases, such as sodium or potassium hydroxide and the like. Where an aqueous base is used, it may be preferable to use a catalytic amount of a phase transfer catalyst such as benzyltriethylammonium chloride, tricaprylylmethylammonium chloride, or the like. Suitable solvents include water or organic solvents such as methylene chloride, chloroform, and the like. The reaction is conducted at a temperature of about 0° C. to about 50° C., preferably from about 5° C. to about 30° C., or for convenience, at ambient temperature. The reaction is generally complete in about 0.5 to about 2 hours. The product, I, is isolated by conventional procedures such as washing, stripping, crystallization, filtration, column chromatography and the like.

UTILITY

The compounds of the present invention are useful in controlling a wide variety of pests.

These compounds are active as fungicides and are particularly effective in controlling a variety of fungi which are deleterious to plant, including plant fungal infections. Some of these compounds are useful in controlling leaf blights caused by organisms such as *Phytophthora infestans*, *Septoria apii*, *Alternaria solani conidia*, and powdery mildews such as that caused by *Erisiphe polygoni*. However, some of the compounds of this invention may be more fungicidally active than others against particular fungi.

In addition, some of the compounds of this invention show antibacterial activity and may inhibit bacterial growth.

When used as fungicides, the compounds of the invention are applied in fungicidally effective amounts to fungi and/or their habitats, such as vegetative hosts and non-vegetative hosts, e.g., animal products. The amount used will, of course, depend on several factors such as the host, the type of fungus, and the particular compound of the invention. As with most pesticidal compounds, the fungicides of the invention are not usually applied full strength, but are generally incorporated with conventional, biologically inert extenders or carriers normally employed for facilitating dispersion of active fungicidal compounds, recognizing that the formulation and mode of application may affect the activity of the fungicide. Thus, the fungicides of the invention may be formulated and applied as granules, as powdery dusts, as wettable powders, as emulsifiable concentrates, as solutions, or as any of several other known types of formulations, depending on the desired mode of application.

Wettable powders are in the form of finely divided particles which disperse readily in water or other dispersants. These compositions normally contain from about 5% to 80% fungicide and the rest inert material, which includes dispersing agents, emulsifying agents and wetting agents. The powder may be applied to the soil as a dry dust, or preferably as a suspension in water. Typical carriers fuller's earth, kaolin clays, silicas, and other highly absorbent, readily wettable, inorganic diluents. Typical wetting, dispersing or emulsifying agents include, for example: the aryl and alkylaryl sulfonates and their sodium salts; alkylamide sulfonates, including fatty methyl taurides; alkylaryl polyether alcohols, sulfated higher alcohols and polyvinyl alcohols; polyethylene oxides; sulfonated animal and vegetable oils; sulfonated petroleum oils; fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises from 1% to 15% by weight of the fungicidal composition.

Dusts are freely flowing admixtures of the active fungicide with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about 50 microns. A typical dust formulation useful herein contains 75% silica and 25% of toxicant.

Useful liquid concentrates include the emulsifiable concentrates, which are homogeneous liquid or paste compositions which are readily dispersed in water or other dispersant, and may consist entirely of the fungicide with a liquid or solid emulsifying agent, or may also contain a liquid carrier such as xylene, heavy aromatic naphthas, isophorone, and other nonvolatile organic solvents. For application, these concentrates are dispersed in water or other liquid carrier, and are normally applied as a spray to the area to be treated.

Other useful formulations for fungicidal applications include simple solutions of the active fungicide in a dispersant in which it is completely soluble at the desired concentration, such as acetone, alkylated naphthalenes, xylene, or other organic solvents. Granular formulations, wherein the fungicide is carried on relatively coarse particles, are of particular utility for aerial distribution or for penetration of cover-crop canopy. Pressurized sprays, typically aerosols wherein the active ingredient is dispersed in finely divided form as a result of vaporization of a low-boiling dispersant solvent carrier, such as the Freons, may also be used. All of those techniques for formulating and applying fungicides are well known in the art.

The percentages by weight of the fungicide may very according to the manner in which the composition is to be applied and the particular type of formulation, but in general comprise 0.5% to 95% of the toxicant by weight of the fungicidal composition.

The fungicidal compositions may be formulated and applied with other active ingredients, including other fungicides, insecticides, nematocides, bactericides, plant-growth regulators, fertilizers, etc.

A further understanding of the invention can be had in the following non-limiting Examples. Wherein, unless expressly stated to the contrary, all temperature ranges refer to the Centigrade system and the term "ambient" or "room temperature" refers to about 20° C. to about 25° C. The term "percent" refers to gram moles. The term "equivalent" refers to a quantity of reagent equal in moles, to the moles of the preceding or succeeding reagent recited in that example in terms of finite moles or finite weight or volume. Also, unless expressly stated to the contrary, geometric isomer and racemic mixtures are used as starting materials and correspondingly, isomer mixtures are obtained as products.

EXAMPLES

Example 1

Preparation of 2-Amino-2-methyl-propionitrile

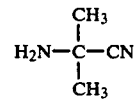

To a stirred solution of 55.45 g (0.88 moles) ammonium formate in 100 ml water, 51.2 g (0.88 moles) acetone were added. The mixture was cooled in an ice bath, while 57 g (0.88 moles) potassium cyanide were spooned in over the period of an hour. The ice bath was removed; stirring of the reaction mixture continued for 3½ hours. The reaction mixture was shaken with 150 ml methylene chloride in a separatory funnel and the phases were separated. The top layer was dried over magnesium sulfate and then distilled over in a Rotovapor ® to give 52.9 g of the above-identified product, as a colorless liquid.

Example 2

Preparation of 2-Methyl-2-(methylsulfonamido)propionitrile

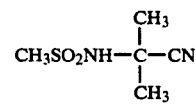

To a stirred mixture of 8.4 g (0.1 mole) 2-amino-2-methylpropionitrile (the product of Example 1), and 10.1 g (0.1 mole) triethylamine in 125 ml methylene chloride, 11.5 g (0.1 mole) methanesulfonyl chloride in 25 ml methylene chloride were added dropwise over about 20 minutes in an exothermic addition reaction. The reaction mixture was stirred 15 minutes, then washed once with 100 ml water, washed twice with 50 ml water, dried over magnesium sulfate, and stripped to give 8.9 g of a brown oil.

The oil was washed with 25 ml hexane. The oil was suspended in 25 ml boiling toluene; enough ethanol was added to give a clear solution. On cooling in an ice bath, crystals were obtained. The resulting crystals were isolated by filtration and then air-dried to give 3.4 g of the above-identified product as beige solid, melting point 72°-74° C.

Elemental analysis for $C_5H_{10}N_2O_2S$ showed: calculated %C 37.04, %H 6.17, and %N 17.2; found %C 37.37, %H 6.41, and %N 18.02.

EXAMPLE 3

Preparation of N-(1,1,2,2-Tetrachloroethylthio)-2-methyl-2-(methylsulfonamido)propionitrile

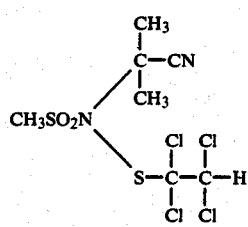

To a stirred mixture of 3.1 g (0.019 moles) 2-methyl-2-(methylsulfonamido)propionitrile (the product of Example 2) and 4.9 g (0.019 mole) 1,1,2,2-tetrachloroethylsulfenyl chloride in 125 methylene chloride, 2.5 g (0.025 moles) triethylamine in 25 ml methylene chloride were dropped in over about 25 minutes. The reaction mixture was stirred about 10 minutes. The reaction mixture was then washed three times with 75 ml water each, dried over magnesium sulfate and stripped to give 6.1 g of a light brown solid. The solid was taken up in 25 ml toluene, treated with decolorizing charcoal, and cooled to give crystals. The crystals were filtered, washed with hexane and air-dried to give 2.4 g of light yellow solids, melting point 120.5° C.-138° C.

The solids were recrystallized twice from hexane containing a little toluene to give 1.6 g of the above-identified product as a white solid, melting point 129° C.-134° C.

Elemental analysis for $C_7H_{10}Cl_4N_2O_2S_2$ showed: calculated %C 23.35, %H 2.78, %N 7.78, and %Cl 39.39; found %C 25.61, %H 3.07, %N 9.16, and %Cl 40.85.

EXAMPLE 4

Preparation of N-Cyanomethyl 4-nitrophenylsulfonamide

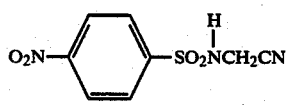

To a stirred solution of 27.8 g (0.3 moles) aminoacetonitrile hydrochloride in 200 ml water, 24 g (0.3 moles) sodium hydroxide (50% aqueous) were added. The resulting mixture was cooled to about 20° C. with an ice bath. The ice bath was removed; then 22.2 g (0.1 mole) 4-nitrobenzenesulfonyl chloride were added. The reaction mixture was stirred 18 hours at ambient temperature. The solids were filtered. The resulting wet cake was crystallized from 50 ml ethanol. The solids were dried in vacuo to give 17.5 g of the above-identified product as a dark-yellow solid, melting point 115°-120° C.

A small portion of the dark yellow solid was recrystallized from toluene containing a small amount of ethanol and given charcoal treatment. A pale-yellow solid, melting point 122°-124° C. was obtained.

Elemental analysis for $C_8H_7N_3O_4S$ showed: calculated %C 39.84, %H 2.94, and %N 17.41; found %C 39.28, %H 3.04, and %N 17.28.

EXAMPLE 5

Preparation of N-Cyanomethyl-N-trichloromethylthio 4-nitrophenylsulfonamide

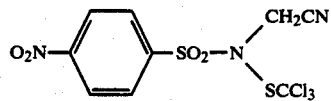

To a stirred mixture of 6.7 g (0.028 moles) N-cyanomethyl 4-nitrophenylsulfonamide (the product of Example 4) and 5.7 g (0.031 mole) trichloromethylsulfenyl chloride in 125 ml methylene chloride, 3.5 g (0.035 mole) triethylamine in 25 ml methylene chloride were dropped in over about 44 minutes. The reaction mixture was washed three times with 75 ml portions of water, dried over magnesium sulfate and stripped to give 10.3 g of brownish solids. The solids were taken up with 25 ml toluene, treated with charcoal and filtered. The filtrate was treated with 25 ml hexane, filtered, and then cooled in an ice bath to give 5.8 g of the above-identified product as a yellow solid, melting point, 123° C.-126° C.

Elemental analysis for $C_9H_6Cl_3N_3O_4S_2$ showed: %C 27.67, %H 1.53, and %N 10.76; found %C 28.87, %H 1.58, and %N 11.47.

EXAMPLE 6

Preparation of N-Cyanomethyl phenylsulfonamide

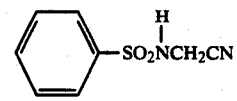

To a stirred solution of 27.8 g (0.3 moles) aminoacetonitrile hydrochloride and 24.0 g (0.3 moles) 50% aqueous sodium hydroxide in 200 ml water, 17.7 g (0.1 mole) benzenesulfonyl chloride were dropped in over about 25 minutes. During the addition, the temperatures of the reaction mixture was kept under 20° C. using an ice bath. After the addition was complete, the ice bath was removed; stirring of the reaction mixture continued for about 30 minutes. The solids which formed were isolated by filtration and were washed with 200 ml water. The resulting beige solids were dissolved in 150 ml methylene chloride, dried over magnesium sulfate and stripped. The resulting white solids were washed with hexane, filtered and air-dried to give 13.9 g of the above-identified product, melting point 81°-83° C.

EXAMPLE 7

Preparation of N-Cyanomethyl-N-(1,1,2,2-tetrachloroethylthio)-phenylsulfonamide

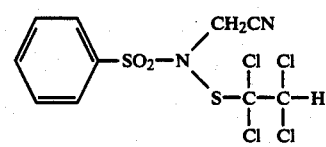

To a stirred solution of 5.0 g (0.025 mole) N-cyanomethyl phenylsulfonamide (the product of Example 6) and 6.0 g (0.026 mole) 1,1,2,2-tetrachloroethyl-sulfenyl chloride in 125 ml methylene chloride, 3.2 g (0.032 mole) triethylamine in 25 ml methylene chloride were dropped in over 35 minutes. The reaction mixture was stirred 20 minutes. The reaction mixture was washed three times with 75 ml portions of water, dried over magnesium sulfate and stripped to give 6.4 g of a brown oil. The oil crystallized when hexane was added to it and the resulting mixture was cooled in an ice bath. The solids were taken up with 25 ml toluene, treated with charcoal and filtered, Hexane, 25 ml, was added to the toluene filtrate, and the resulting mixture was cooled in an ice bath to give 2.3 g of yellow crystals, melting point 89°–101° C. The crystals were recrystallized from a mixture of 25 ml hexane and 5 ml toluene. The filtrate was cooled in an ice bath to give 0.8 g of the above-identified product as a white solid, melting point 106° C.–108° C.

Elemental analysis for $C_{10}H_8Cl_4N_2O_2S_2$ showed: calculated %C 30.48, %H 2.03, and %N 7.11; found %C 32.14, %H 2.28, and %N 7.72.

EXAMPLE 8

Preparation of 2-Amino-2-(3-thienyl)-propionitrile hydrochloride

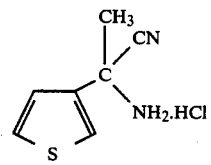

A mixture of 5 g (0.04 mole) 3-acetothiophene, 4 g (0.08 mole) sodium cyanide, 5 g (0.08 mole) ammonium formate, 10 ml 30% ammonium hydroxide and 2 ml methanol was stirred at ambient temperature in a sealed bottle for 7 days. The mixture was extracted with methylene chloride; evaporation of the methylene chloride gave 5 g of crude product as an oil. The oil was dissolved in ether; hydrogen chloride gas was bubbled through the solution to precipitate the product as the hydrochloride salt. Filtration gave 6 g of the above-identified hydrochloride salt.

EXAMPLE 9

Preparation of 2-(3-Thienyl)-2-(methylsulfonamido)propionitrile

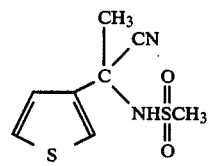

To a mixture of 2.7 g (0.0143 mole) 2-amino-2-(3-thienyl)-propionitrile hydrochloride (the product of Example 8) in 50 ml methylene chloride, 3.6 g (5 ml [0.036 mole]) triethylamine were added, followed by 2 g (1.4 ml [0.018 mole]) methanesulfonyl chloride. The reaction mixture was stirred at room temperature for three hours. The reaction mixture was then washed with saturated sodium bicarbonate and brine, dried over sodium sulfate and stripped to give the above-identified product which was used in Example 10 without further purification.

EXAMPLE 10

Preparation of N-(1,1,2,2-Tetrachloroethylthio)-2-(3-thienyl)-2-(methylsulfonamido)propionitrile

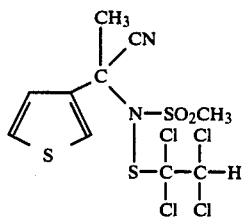

To a stirred mixture of 2.1 g (0.0091 mole) 2-(3-thienyl)-2-(methylsulfonamido)propionitrile (the product of Example 9) and 2.6 g (0.01 mole) 1,1,2,2-tetrachloroethylsulfenyl chloride in 50 ml methylene chloride, a mixture of 0.9 g (0.011 mole) 50% sodium hydroxide in 10 ml water was added. To that mixture, a catalytic amount of benzyltriethylammonium chloride (about 0.1 g) was added. The reaction mixture was stirred at ambient temperature for about one hour. The reaction mixture was washed with brine, dried over sodium sulfate, and stripped to yield 3 g of the above-identified product, as an off-white solid.

Elemental analysis for $C_{10}H_{10}Cl_4N_2O_2S_3$ showed: calculated %C 28.04, %H 2.34, and %N 6.54; found %C 28.43, %H 2.51, and %N 6.62.

EXAMPLE 11

Preparation of 2-Amino-2-phenyl-propionitrile hydrochloride

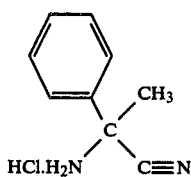

To a stirred solution of 3.8 g (0.058 mole) potassium cyanide in 7 ml water, a solution of 3.6 g (0.066 mole) ammonium chloride in 8 ml water was added. To the resulting mixture, 3.5 g (3.9 ml [0.10 mole]) ammonium hydroxide were added, followed by 7 g (0.058 mole) acetophenone dissolved in 10 ml methanol. The reaction mixture was heated at about 45°–55° C. for 18 hours. The black mixture was poured into water and extracted with methylene chloride. The methylene chloride extract was washed 4 times with water, dried over sodium sulfate, filtered and stripped. The residue was dissolved in ether. Hydrogen chloride gas was bubbled through the solution to precipitate 2 g of the above-identified hydrochloride salt, as a yellow solid.

EXAMPLE 12

Preparation of
2-Phenyl-2-(methylsulfonamido)propionitrile

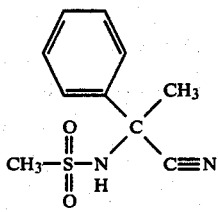

To a mixture of 2 g (0.0109 mole) 2-amino-2-phenyl-propionitrile hydrochloride (the product of Example 11) in methylene chloride (about 50 ml), 2.6 g (0.0218 mole) 4-dimethylaminopyridine was added, followed by 1.3 g (0.0109 mole) methanesulfonyl chloride in 10 ml methylene chloride in an exothermic addition. The reaction mixture was stirred for 2 hours at room temperature. The reaction mixture was poured into 100 ml ice water. The layers were separated using a separatory funnel. The organic (methylene chloride) phase was washed twice with water, dried over magnesium sulfate, filtered and stripped to give 2 g of the above-identified product as an orange slush.

EXAMPLE 13

Preparation of
N-(1,1,2,2-Tetrachloroethylthio)-2-phenyl-2-(methylsulfonamido)propionitrile

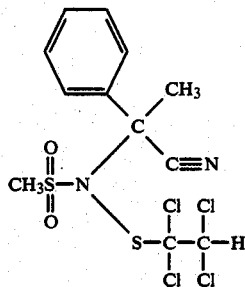

To a mixture of 2 g (0.0089 mole) 2-phenyl-2-(methylsulfonamido)propionitrile (the product of Example 12) in 35 ml methylene chloride, 0.99 g (1.4 ml [0.0098 mole]) triethylamine was added. To the resulting mixture, 2.3 g (0.0098 mole) 1,1,2,2-tetrachloroethylsulfenyl chloride in 7 ml methylene chloride was added dropwise. The reaction mixture was stirred at room temperature for three hours and then poured into water. The layers were phase separated. The organic (methylene chloride) layer was washed three times with water, dried, filtered and stripped. Precipitation of the residue from hexane/ether gave yellow fluffy solids which were chromatographed on silica gel using 10% ethyl acetate/hexane as eluent to yield 1.2 g of the above-identified product as a white solid.

Elemental analysis for $C_{12}H_{12}Cl_4N_2O_2S_2$ showed: calculated %C 34.12, %H 2.84, and %N 6.64; found %C 34.96, %H 2.89, and %N 6.7.

EXAMPLE 14

Preparation of 1-Amino-1-cyano-cyclopentane hydrochloride

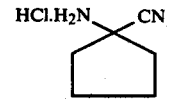

A mixture of 84 g (1 mole) cyclopentanone, 63 g (1 mole) ammonium formate and 525 ml water were stirred together to give a clear solution. To that solution, 65 g (1 mole) potassium cyanide were spooned in over 10 minutes with a little heat evolution; an oily phase began to separate. The reaction mixture was stirred at ambient temperature for 24 hours. The upper layer was separated and weighed about 50 g; it was diluted to 400 ml with toluene and then dried over magnesium sulfate. The toluene mixture was saturated with dry hydrogen chloride gas, giving separation of solids (a precipitate). The solids (precipitate) were filtered, washed with toluene and hexane, and dried at 60° C. in a vacuum oven to give 29 g of the above-identified product, as a beige solid which decomposed at 155°-160° C. when heated rapidly.

EXAMPLE 15

Preparation of
1-Cyano-1-(methylsulfonamido)cyclopentane

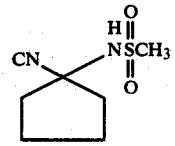

To a stirred mixture of 20.2 g (0.2 mole) triethylamine and 200 ml chloroform cooled in an ice bath, 14.7 g (0.1 mole) 1-amino-1-cyanocyclopentane hydrochloride (the product of Example 14) were spooned in over ten minutes to give a red solution. To that mixture, 11.5 g (0.1 mole) methanesulfonyl chloride in 25 ml chloroform were added dropwise over 30 minutes. The reaction mixture was stirred 30 minutes. The reaction mixture was washed with 25 ml concentrated hydrochloric acid which had been diluted to 50 ml with ice water. The layers were phase separated. The organic layer was washed twice with 50 ml ice water, dried over magnesium sulfate and stripped to give 13 g of the above-identified amber oily product.

EXAMPLE 16

Preparation of
N-(1,1,2,2-tetrachloroethylthio)-1-cyano-1-(methylsulfonamido)cyclopentane

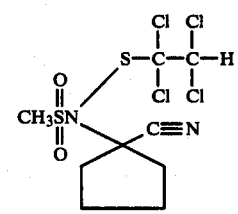

To a stirred mixture of 7.2 g (0.038 mole) 1-cyano-1-(methylsulfonamido)cyclopentane (the product of Example 15) and 9.0 g (0.038 mole) 1,1,2,2-tetrachloroethylsulfenyl chloride in 125 ml methylene chloride, 4.7 g (0.046 mole) triethylamine in 25 ml methylene chloride were added dropwise over 25 minutes. The reaction mixture was stirred 15 minutes. The reaction mixture was washed three times with 50 ml ice water, dried over magnesium sulfate and stripped to give crystals. The crystals were recrystallized twice from toluene to give 6.3 g of the above-identified product, as white crystals, melting point 143°–145° C.

Elemental analysis for $C_9H_{12}Cl_4N_2O_2S_2$ showed: calculated %C 27.98, %H 3.13, and %N 7.26; found %C 28.01, %H 3.36, and %N 6.7.

EXAMPLE 17

Preparation of 2-Methyl-2-(n-butylsulfonamido)propionitrile

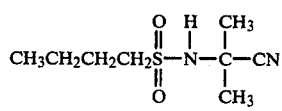

To a stirred mixture of 8.4 g (0.1 mole) 2-amino-2-methyl-propionitrile and 12.2 g (0.1 mole) 4-dimethylaminopyridine in 125 ml chloroform, 15.7 g (0.1 mole) 1-butanesulfonyl chloride in 25 ml chloroform were added dropwise over 20 minutes, with evolution of heat and separation of solids. The reaction mixture was refluxed 2.5 hours. After cooling to room temperature, the reaction mixture was washed with 25 ml concentrated hydrochloric acid which had been diluted with 25 ml water. The layers were phase separated. The organic layer was washed twice with 50 ml ice water, dried over magnesium sulfate and stripped to give 8.0 g of the above-identified product, as a dark red oil.

EXAMPLE 18

Preparation of N-(1,1,2,2-Tetrachloroethylthio)-2-methyl-2-(n-butylsulfonamido)propionitrile

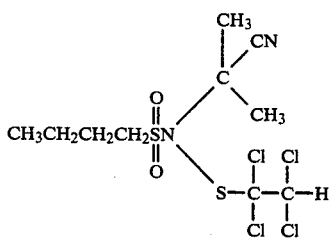

To a stirred mixture of 8.0 g (0.04 mole) 2-methyl-2-(n-butylsulfonamido)propionitrile (the product of Example 17) and 9.2 g (0.04 mole) 1,1,2,2-tetrachloroethylsulfenyl chloride in 125 ml methylene chloride, 4.8 g (0.05 mole) triethylamine in 25 ml methylene chloride were added dropwise over twenty minutes. The reaction mixture was stirred overnight at ambient temperature, washed three times with 50 ml ice water, dried over magnesium sulfate and stripped to yield 13.5 g of brown oil. The oil was taken up in 75 hexane, and treated with charcoal. Cooling gave 2.3 g of the above-identified product as a beige solid, melting point 104°–106° C.

Elemental analysis for $C_{18}H_{16}Cl_4N_2O_2S_2$ showed: calculated %C 29.83, %H 4.81, and %N 6.96; found %C 29.73, %H 4.17, %N 7.47.

EXAMPLE 19

Preparation of 2-Methoxyethanesulfonyl chloride

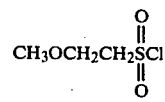

(a) A mixture of 100 g (1.06 mole) 2-chloroethyl methyl ether, 133 g (1.06 mole) sodium sulfite and 300 ml water was mildly refluxed over the weekend for about 72 hours. The solution was decanted to remove a small amount of semi-solid which had separated, and then stripped. The resulting white solid was washed with ethyl ether/toluene (80/20) and then dried.

(b) The dry white powder from step (a) was added in small portions to about 250 ml phosphorus oxychloride. The resulting heterogeneous mixture was stirred overnight at room temperature, and then refluxed about 8 hours. About 300 ml methylene chloride was added; the resulting mixture was thoroughly mixed and then filtered. The filtrate was stripped. Ethyl acetate, about 200 ml, was added to the residue and the mixture was then added to about 300 ml cracked ice. The ice was allowed to melt. Additional ethyl acetate was added to bring the ethyl acetate phase to the top. (Initially, the water phase stayed at the top.) The ethyl acetate solution was separated. The organic phase was washed once again with about 200 ml water and once with about 50 ml saturated sodium chloride solution, dried over magnesium sulfate, filtered and stripped to give 122 g of the above-identified product.

EXAMPLE 20

Preparation of 2-Methyl-2-(2'-methoxyethylsulfonamido)propionitrile

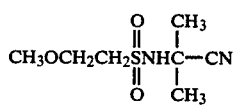

To a stirred mixture of 10 g (0.12 mole) 2-amino-2-methyl-propionitrile and 12.1 g (0.12 mole) triethylamine in about 200 ml methylene chloride cooled by an ice bath, 18.8 g (0.12 moles) 2-methoxyethane sulfonyl chloride (the product of Example 19) in 15 ml methylene chloride were added dropwise. The reaction mixture was then stirred at room temperature over the weekend. The reaction mixture was washed three times with equal amounts (about 200 ml) water, dried over magnesium sulfate, filtered and stripped to give an oil. The oil was recrystallized from ethyl ether/petroleum ether to give 15.0 g of the above-identified product, melting point 58°–60° C.

Elemental analysis for $C_7H_{14}N_2O_3S$ showed: calculated %C 40.76, %H 6.84, and %N 13.58; found %C 41.55, %H 7.39, and %N 13.87.

EXAMPLE 21

Preparation of N-(1,1,2,2-Tetrachloroethylthio)-2-methyl-2-(2'-methoxyethylsulfonamido)propionitrile

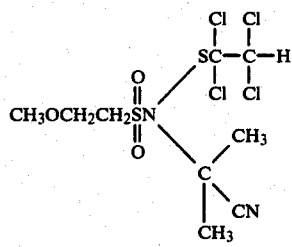

To a stirred mixture of 4 g (0.019 mole) 2-methyl-2-(2'-methoxyethylsulfonamido)propionitrile (the product of Example 20), 4.6 g (0.019 mole) 1,1,2,2-tetrachloroethylsulfenyl chloride and 0.5 g benzyltriethylammonium chloride in 150 ml methylene chloride, cooled by an ice bath, 1.6 g (0.019 mole) 50% sodium hydroxide was added dropwise. The reaction mixture was then stirred at room temperature overnight. The reaction mixture was washed three times with equal portions (about 150 ml) of water, dried over magnesium sulfate, filtered and stripped. Recrystallization of the residue from ethyl ether gave 4.2 g of the above-identified product, as a brown solid.

Element analysis for $C_9H_{14}Cl_4N_2O_3S_2$ showed: calculated %C 26.75, %H 3.49, and %N 6.93; found %C 29.41, %H 4.55, and %N 7.7.

EXAMPLE 22

Preparation of 2-Methyl-2-(ethenylsulfonamido)propionitrile

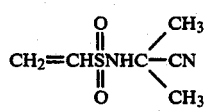

To a stirred mixture of 8.0 g (0.049 mole) 2-chloroethylsulfonyl chloride in 200 ml methylene chloride, cooled by an ice bath, 8.3 g (0.098 mole) 2-amino-2-methyl-propionitrile were added dropwise. The reaction mixture was then stirred at room temperature overnight. The reaction mixture was washed twice with equal portions (about 200 ml) water, dried over magnesium sulfate, filtered and stripped to give a semi-solid. The semi-solid was triturated with ethyl ether/acetone and filtered to remove salts. The filtrate was stripped to give 7.9 g of the above-identified product as an amber oil.

Example 23

Preparation of N-(1,1,2,2-Tetrachloroethylthio-2-methyl-2-(ethenylsulfonamido)propionitrile

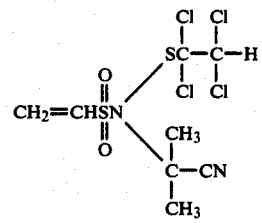

To a stirred mixture of 3.9 g (0.02 mole) 2-methyl-2-(ethenylsulfonamido)propionitrile (the product of Example 22), 5.0 g (0.02 mole) 1,1,2,2-tetrachloroethylsulfenyl chloride and 0.5 g benzyltriethylammonium chloride in 150 ml methylene chloride, cooled by an ice bath, 10 ml water was added; then 1.6 g (0.02 moles) 50% sodium hydroxide was added dropwise. The reaction mixture was stirred and allowed to come to room temperature overnight. The reaction mixture was washed twice with equal amounts (about 150 ml) water, dried over magnesium sulfate, filtered and stripped. The solid residue was washed with petroleum ether and then dried to give 3.3 g of the above-identified product as a beige solid.

Elemental analysis for $C_8H_{10}Cl_4N_2O_2S_2$ showed: calculated %C 25.81, %H 2.71, and %N 7.52; found %C 26.24, %H 2.89, and %N 8.61.

Example 24

Preparation of Sodium 2-carboethoxyethyl sulfonate

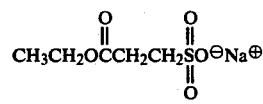

A mixture of 52 g (0.29 moles) ethyl 3-bromopropionate and 36.1 g (0.29 moles) anhydrous sodium sulfite in 150 ml water was refluxed for about 16 hours. The reaction mixture was stripped. The residue was washed with acetone and ethyl ether, stripped, and dried in a vacuum oven to give 90.5 g of the above-identified product.

Example 25

Preparation of 2-Carboethoxyethylsulfonyl chloride

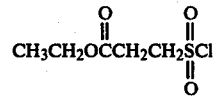

To a stirred mixture of 90.5 g (0.44 moles) sodium 2-carboethoxyethyl sulfonate (the product of Example 26) in 300 ml chloroform, 92 g (0.44 moles) phosphorus pentachloride was added in small portions, maintaining the temperature of the reaction mixture below 40° C. during the addition. The reaction mixture was refluxed for about 6 hours, and then filtered. Nitrogen was bubbled through the solution to remove excess hydrogen chloride gas. Stripping of the solvent gave 28.4 g of the above-identified product.

Example 26
Preparation of N-(2-Cyano-2-propyl)-vinylsulfonamide

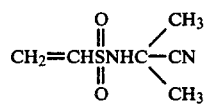

To a stirred solution of 39.3 g (0.241 mole) 2-chloroethylsulfonyl chloride in 250 ml methylene chloride at 0° C. under $N_2$, 63.09 g (0.75 moles) 2-amino-2-methylpropionitrile was added dropwise over several hours. The solution was allowed to come to room temperature overnight and then was heated to reflux for one hour, was cooled to room temperature and filtered. The filtrate was evaporated to give 44 g of a yellow oil. One half, 22 g, of the oil was chromatographed to give 21 g of the above-identified product.

Example 27
Preparation of N-(2-Cyano-2-propyl)-2-methylthioethylsulfonamide

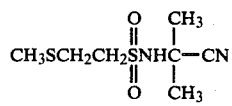

To a solution of 8.2 g (0.0470 moles) N-(2-cyano-2-propyl)-vinylsulfonamide (the product of Example 26) in 30 ml methanol, 32 ml of a 1.5M solution of methanethiol was added over 5 minutes. A small amount (a few mg) of potassium carbonate was added to the mixture and it was stirred overnight at room temperature. The reaction mixture was warmed to about 30° C., more methanethiol/methanol solution (about 10 ml) was added, and the resulting mixture was stirred at 30° C. for four hours. The mixture was acidified with 10% hydrochloric acid and then evaporated to afford 10.0 g of a pale yellow oil. The oil was dissolved in methylene chloride, filtered and evaporated to dryness. The residue was purified by flash chromatography with 30% hexane in ethyl acetate to give 9.3 g of the above-identified product, as a colorless oil which crystallized upon standing.

Example 28
Preparation of N-(1,1,2,2-Tetrachloroethylthio)-N-(2-cyano-2-propyl)-2-methylthioethylsulfonamide

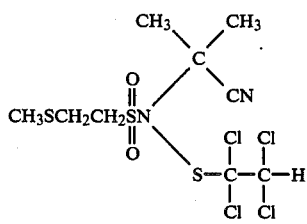

To a stirred mixture of 3.53 g (0.0159 moles) N-(2-cyano-2-propyl)-2-(methylthio)ethylsulfonamide (the product of Example 27), 4.15 g of 89.9% 1,1,2,2-tetrachloroethylsulfenyl chloride (3.74 g [0.0159] moles) and about 1 g benzyltriethylammonium chloride in 25 ml methylene chloride, 0.8 g (0.02 l mole) sodium hydroxide in 5 ml water was added. The reaction mixture was stirred at room temperature for 18 hours. The layers were separated using a separatory funnel. The methylene chloride layer was washed three times with 30 ml water, dried and concentrated on a rotovap to about 20 ml. Hexane was added to the solution until turbidity. The mixture was warmed until clear. Cooling of the mixture gave a white powder which was isolated by filtration and then washed with hexane to give 2.4 g of crude product. A second crop of 1.8 g of crude product was obtained from the filtrate. The two crops were combined and recrystallized from ethanol to give 2.2 g of the above-identified product as a solid, melting point 83°–84° C. A second crop of 1.1 g solid was obtained.

Example 29
Preparation of N-(2-Cyano-2-propyl)-2-methylsulfinylethylsulfonamide

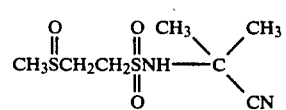

To a stirred solution of 4.27 g (0.020 moles) sodium metaperiodate in 40 ml water which had been cooled to about 0° C. in an ice bath, 4.10 g (0.0184 mole) N-(2-cyano-2-propyl)-2-methylthioethylsulfonamide (the product of Example 27) in about 10 ml methanol was added slowly. Initially, the mixture was homogeneous, but after the addition was complete (after about three minutes), a thick precipitate formed. Additional methanol (15 ml) and water (60 ml) was added, thinning the precipitate to allow stirring. The mixture was stirred overnight in a slowly melting ice bath and then filtered. The solid was washed with methylene chloride. The filtrate was washed three times with 50 ml methylene chloride. The methylene chloride fractions were combined and evaporated to dryness to give 2.2 g of crude product, as a white solid. Recrystallization from ethanol gave 1.6 g of the above-identified product as a solid, melting point 142°–144° C.

The aqueous fractions were evaporated to dryness to give 4.7 g solids. The solids were extracted with about 100 ml boiling methylene chloride. The methylene chloride was filtered; the filtrate was evaporated to give an additional 1.3 g of the above-identified product.

Elemental analysis for $C_7H_{14}N_2O_3S_2$ showed: calculated %C 35.28; %H 5.92, %N 11.76, and %S 26.91; found %C 35.95, %H 6.42, %N 12.41, and %S 27.08.

Example 30
Preparation of N-(1,1,2,2-tetrachloroethylthio)-N-(2-cyano-2-propyl)-2-methylsulfinylethylsulfonamide

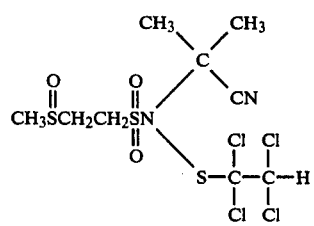

A stirred mixture of 2.38 g (0.01 moles) N-(2-cyano-2-propyl)-2-methylsulfinylethylsulfonamide (Example 29), 2.85 g (0.0109 moles) of 89.9% technical 1,1,2,2-tetrachloroethylsulfenyl chloride and a catalytic amount (about 0.25 g) of benzyltriethylammonium chloride in 30 ml methylene chloride was warmed until a solution was obtained. To that mixture, 0.96 g of a 50% solution of sodium hydroxide which had been diluted to 5 ml was added at once. The reaction mixture was stirred at reflux for four hours, then cooled and poured into a separatory funnel. The methylene chloride layer was separated, washed three times with 25 ml water, dried and evaporated to about 10 ml. The oily residue was transferred to a 50 ml Erlenmeyer flask and then diluted with about 25 ml hexane. The white precipitate which formed was recovered by filtration and washed with hexane to give 2.85 g of a white powder. Chromatography on silica gel, followed by recrystallization from ethanol gave 1.7 g of the above-identified product as white crystals, melting point 119°–120° C.

Elemental analysis for $C_9H_{14}N_2O_3S_3Cl_4$ showed: calculated %C 24.78, %H 3.23, and %N 6.42, %S 22.05, and %Cl 32.51; found %C 24.76, %H 3.39, %N, 6.59, and %Cl 32.0.

Example 31

Preparation of 1-Acetylthio-2-methylsulfonylethane

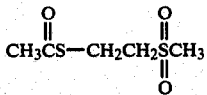

To a stirred solution of 53.2 g (0.5 mole) methylvinylsulfone and 1 ml triethylamine in 50 ml methanol, 38.06 g [35.75 ml (0.5 mole)] thioacetic acid was added dropwise over 15 minutes. During the addition, the temperature was maintained between 30°–40° C. with an ice bath. The mixture was stirred overnight at room temperature; then the solvent was removed using a rotovap to give a yellow-red oil which solidified upon cooling. The residue was dissolved in 150 ml of hot ethyl acetate; then 100 ml hexane was added. With cooling of the solution in an ice bath, fine white needle crystals formed. The crystals were recovered by filtration, were washed with cold 1:1 ethyl acetate:hexane and air-dried to give 35.28 g of the above-identified product as a crystalline solid, melting point 57°–59° C. A second crop of 29.13 g crystals melting point 57°–60° C. was obtained to give a total of 64.41 g of the above-identified product.

Example 32

Preparation of 2-(Methylsulfonyl)ethylsulfonyl chloride

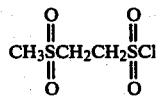

Chlorine gas, about 14 g, (about 0.197 moles) was slowly bubbled into a stirred mixture of 9.11 g (0.05 moles) 1-acetylthio-2-methylsulfonylethane (the product of Example 31), 100 ml glacial acetic acid and 5 ml water. As the temperature of the mixture increased from 20° C. to 40° C., a voluminous white precipitate formed making a very thick suspension. An additional 50 ml acetic acid was added to dilute the suspension. The white solid slowly went back into solution as bubbling of the chlorine gas continued. Nitrogen gas was bubbled through the solution as it was allowed to come to room temperature. The reaction mixture was then cooled to 15° C. in an ice bath. A white precipitate formed. The precipitate was collected by filtration, washed with ethanol and ethyl ether and then air-dried to give 4.95 g of the above-identified product, melting point 118°–121° C.

Example 33

Preparation of N-(2-Cyano-2-propyl)-2-(methylsulfonyl)-ethylsulfonamide

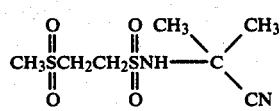

To a stirred solution of 5.00 g (24.2 mmoles) 2-(methylsulfonyl)ethylsulfonyl chloride (Example 32) in 50 ml dry tetrahydrofuran, a solution of 2.11 g (0.025 moles) 2-amino-2-methyl-propionitrile and 2.5 g (0.025 moles) triethylamine in 20 ml dry tetrahydrofuran were added dropwise over 13 minutes. During the course of the addition, the temperature of the mixture rose from 19° C. to 38° C. and a white precipitate formed. After the mixture cooled to room temperature, it was filtered. The solid, inorganic salts, was washed with tetrahydrofuran and ethyl ether. The filtrate and washings were stripped using a rotovap to give 8.2 g of a sticky white solid. Recrystallization of the solid from boiling ethanol gave 3.94 g of the above-identified product, melting point 151°–153° C.

Example 34

Preparation of N-(1,1,2,2-Tetrachloroethylthio)-N-(2-cyano-2-propyl)-cyano-2-(methylsulfonyl)ethylsulfonamide

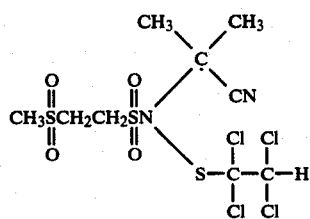

To a stirred suspension of 2.83 g (0.011 moles) N-(2-cyano-2-propyl)-2-(methylsulfonyl)ethylsulfonamide (the product of Example 33) and 2.61 g (0.011 moles) tetrachloroethylsulfenyl chloride in 40 ml tetrahydrofuran, a solution of 1.5 g (0.015 mole) triethylamine in 10 ml tetrahydrofuran was added dropwise over five minutes. During the addition, the temperature of the reaction mixture rose from about 24° C. to about 35° C. and a precipitation formed. The mixture was stirred an additional half hour and then filtered. The solids were washed with tetrahydrofuran and then discarded. The filtrate was evaporated to dryness to give 7 g of a sticky white solid. The solid was taken up in about 100 ml methylene chloride. The mixture was filtered to remove solids. The methylene chloride filtrate was washed with water, dried over calcium sulfate and stripped to give 3.4 g of an oil. The oil was taken up in hot ethanol. Upon cooling of the ethanol, white crystals formed which were filtered, washed with ethanol and air-dried to give 2.0 g of the above-identified product, melting point 120°–123° C.

An additional crop of 200 mg of product (melting point 121°–123° C.) was obtained by concentration of the filtrate and washings and then crystallization.

Elemental analysis for $C_9H_{14}N_2Cl_4O_4S_3$ showed: calculated %C 23.90, %H 3.12, %N 6.20, %cl 31.36, and %S 21.27; found %C 23.92, %H 3.26, %N 7.02, %Cl 31.9, and %S 22.4.

Example 35

Preparation of 2-Methyl-2-(3-chloropropylsulfonamido)-propionitrile

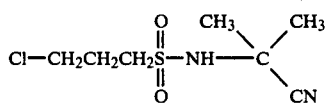

To a stirred mixture of 9.90 g (0.05 mole) 3-chloropropane sulfonyl chloride and 4.71 g (0.056 mole) 2-amino-2-methyl-propionitrile in 100 ml methylene chloride at 0° C., 5.66 g (0.056 mole) triethylamine as a 10% solution in methylene chloride was added very slowly. The reaction mixture was allowed to stir overnight in the gradually melting ice bath. The reaction mixture was washed three times with 50 ml water. The organic layer was dried over calcium sulfate and evaporated to give 9.90 g of the above-identified product as a brown oil.

Example 36

Preparation of N-(1,1,2,2-Tetrachloroethylthio)-N-(2-cyano-2-propyl)-3-chloropropylsulfonamide

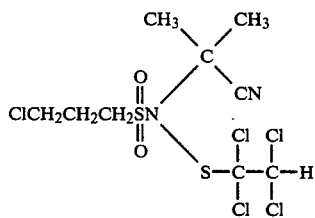

To a stirred mixture of 2.25 g (0.01 mole) 2-methyl-2-(3-chloropropylsulfonamido)propionitrile (the product of Example 35) and 2.87 g (0.011 mole) tetrachloroethylsulfenyl chloride with 0.1 g benzyltriethylammonium chloride in 100 ml methylene chloride, 0.48 g [(0.012 mole) 0.96 g as a 50% weight/weight solution] sodium hydroxide dissolved in 20 ml water was added slowly. The reaction mixture was stirred for three hours. The mixture was washed three times with 100 ml water. The organic layers were dried over calcium sulfate and evaporated to give a dark brown oil which crystallized upon standing overnight. The crystals were washed with hexane to give the above-identified product, as a brown solid, melting point 68°–71° C.

Elemental analysis for $C_9H_{13}N_2S_2O_2Cl_5$ showed: calculated %C 25.58, %H 3.10, %N 6.63, %S 15.17, and %Cl 41.95; found %C 25.85, %H 3.2, %N 7.09, %S 15.0, and %Cl 43.5.

Compounds made in accordance with the methods disclosed in the Detailed Description of the Invention and with Examples 1 to 36 are found in Tables I and II.

In addition, by following the procedures disclosed in the Detailed Description of the Invention and in Examples 1 to 36 and using the appropriate starting materials and reagents, the following compounds are made:

N-(1,1,2,2-tetrachloroethylthio)-2-methyl-2-(isopropylsulfonamido)propionitrile;

N-(1,1,2,2-tetrachloroethylthio)-2-methyl-2-(2-methylhexylsulfonamido)propionitrile;

N-(1,1,2,2-tetrachloroethylthio)-2-methyl-2-(n-octylsulfonamido)propionitrile;

N-(1,1,2,2-tetrachloroethylthio)-2-methyl-2-(proparglysulfonamido)propionitrile;

N-(1,1,2,2-tetrachloroethylthio)-2-methyl-2-(2-cyclopropylsulfonamido)propionitrile;

N-cyanomethyl-N-(1,1,2,2-tetrachloroethylthio)methylsulfonamide;

N-cyanomethyl-N-(1,1,2,2-tetrachloroethylthio)propylsulfonamide;

N-cyanomethyl-N-(1,1,2,2-tetrachloroethylthio)isopropylsulfonamide;

N-cyanomethyl-N-(1,1,2,2-tetrachloroethylthio)hexylsulfonamide;

N-cyanomethyl-N-(1,1,2,2-tetrachloroethylthio)ethylsulfonamide;

N-(1,1,2,2-tetrachloroethylthio)-2-(ethylsulfonamido)propionitrile;

N-(1,1,2,2-tetrachloroethylthio)-2-(isopropylsulfonamido)propionitrile;

N-(1,1,2,2-tetrachloroethylthio)-2-(n-hexylsulfonamido)propionitrile;

N-trichloromethylthio-2-methyl-2-(isopropylsulfonamido)propionitrile;

N-trichloromethylthio-2-methyl-2-(n-hexylsulfonamido)propionitrile;

N-trichloromethylthio-2-(methylsulfonamido)propionitrile;

N-trichloromethylthio-2-(ethylsulfonamido)propionitrile;

N-trichloromethylthio-2-(isopropylsulfonamido)propionitrile;

N-trichloromethylthio-2-(n-hexylsulfonamido)propionitrile;

N-cyanomethyl-N-trichloromethylthiomethylsulfonamide;

N-cyanomethyl-N-trichloromethylthioethylsulfonamide;

N-cyanomethyl-N-trichloromethylthioisopropylsulfonamide;

N-cyanomethyl-N-trichloromethylthio-(2-methylhexylsulfonamide;

N-dichlorofluoromethylthio-2-methyl-2-(methylsulfonamido)propionitrile;

N-dichlorofluoromethylthio-2-methyl-2-(ethylsulfonamido)propionitrile;

N-dichlorofluoromethylthio-2-methyl-2-(ethylsulfonamido)propionitrile;

N-dichlorofluoromethylthio-2-methyl-2-(isopropylsulfonamido)proprionitrile;

N-dichlorofluoromethylthio-2-methyl-2-(n-hexylsulfonamido)propionitrile;

N-dichlorofluoromethylthio-2-(methyl-sulfonamido)propionitrile;

N-dichlorofluoromethylthio-2-(ethylsulfoanmido)propionitrile;

N-dichlorofluoromethylthio-2-(isopropylsulfonamido)-propionitrile;
N-dichlorofluoromethylthio-2-(n-octylsulfonamido)-propionitrile;
N-cyanomethyl-N-dichlorofluoromethylthio-methylsulfonamide;
N-cyanomethyl-N-dichlorofluoromethylthio-ethylsulfonamide;
N-cyanomethyl-N-dichlorofluoromethylthio-isopropylsulfonamide;
N-cyanomethyl-N-dichlorofluoromethylthio-tert-butylsulfonamide;
N-cyanomethyl-N-dichlorofluoromethylthio-2,2-dimethyloctylsulfonamide;
N-cyanomethyl-N-dichlorofluoromethylthio-phenylsulfonamide;
N-cyanomethyl-N-dichlorofluoromethylthio-4-nitrophenylsulfonamide;
N-cyanomethyl-N-dichlorofluoromethylthio-benzylsulfonamide;
N-cyanomethyl-N-(1,1,2,2-tetrachloroethylthio)-but-2-enylsulfonamide;
N-cyanomethyl-N-(1,1,2,2-tetrachloroethylthio)-pent-3-ynylsulfonamide;
N-cyanomethyl-N-(1,1,2,2-tetrachloroethylthio)-1-methylcyclopropylsulfonamide;
N-trichlorovinylthio-2-methyl-2-(methylsulfonamido)-propionitrile;
N-trichlorovinylthio-2-methyl-2-(ethylsulfonamido)-propionitrile;
N-trichlorovinylthio-2-methyl-2-(isopropylsulfonamido)propionitrile;
N-trichlorovinylthio-2-methyl-2-(phenylsulfonamido)-propionitrile;
N-trichlorovinylthio-2-(methylsulfonamido)propionitrile;
N-trichlorovinylthio-2-(ethylsulfonamido)propionitrile;
N-trichlorovinylthio-2-(isopropylsulfonamido)propionitrile;
N-cyanomethyl-N-trichlorovinylthio-phenylsulfonamide;
N-cyanomethyl-N-trichlorovinylthio-benzylsulfonamide;
N-cyanomethyl-N-trichlorovinylthio-cyclohexylsulfonamide;
N-cyanomethyl-N-trichlorovinylthio-2,2-dimethylpentylsulfonamide;
N-(2-fluoro-1,1,2,2-tetrachloroethylthio)-2-methyl-2-(ethylsulfonamido)propionitrile;
N-(2-fluoro-1,1,2,2-tetrachloroethylthio)-2-methyl-2-(ethylsulfonamido)propionitrile;
N-(2-fluoro-1,1,2,2-tetrachloroethylthio)-2-methyl-2-(isopropylsulfonamido)propionitrile;
N-(2-fluoro-1,1,2,2-tetrachloroethylthio)-2-methyl-2-(phenylsulfonamido)propionitrile;
N-(2-fluoro-1,1,2,2-tetrachloroethylthio)-2-(methylsulfoanmido)propionitrile;
N-(2-fluoro-1,1,2,2-tetrachloroethylthio)-2-(ethylsulfonamido)propionitrile;
N-(2-fluoro-1,1,2,2-tetrachloroethylthio)-2-(isopropylsulfonamido)propionitrile;
N-(2-fluoro-1,1,2,2-tetrachloroethylthio)-2-(benzylsulfonamido)propionitrile;
N-(2-fluoro-1,1,2,2-tetrachloroethylthio)-2-(phenylsulfonamido)propionitrile;
N-cyanomethyl-N-(2-fluoro-1,1,2,2-tetrachloroethylthio)-methylsulfonamide;
N-cyanomethyl-N-(2-fluoro-1,1,2,2-tetrachloroethylthio)-ethylsulfonamide;
N-cyanomethyl-N-(2-fluoro-1,1,2,2-tetrachloroethylthio)-isopropylsulfonamide;
N-cyanomethyl-N-(2-fluoro-1,1,2,2-tetrachloroethylthio)-decylsulfonamide;
N-cyanomethyl-N-(2-fluoro-1,1,2,2-tetrachloroethylthio)-phenylsulfonamide;
N-cyanomethyl-N-(2-fluoro-1,1,2,2-tetrachloroethylthio)-4-nitrophenylsulfonamide;
N-cyanomethyl-N-(2-fluoro-1,1,2,2-tetrachloroethylthio)-benzylsulfonamide.

Example A

Bacterial Inhibition

Compounds of this invention were evaluated for in vitro bactericidal effectiveness by means of a bacterial inhibition test. This test is designed to measure the antibacterial activity of compounds in terms of degree of inhibition of bacterial multiplication. The representative bacteria used were *Erwinia amylovora, Pseudomonas syringae* and *Xanthomonas vesicatoria*. Each compound to be tested was dissolved in acetone to give a 500 ppm concentration. Agar plates were inoculated using a micro sprayer with an suspension of the particular bacteria shortly (3 to 5 seconds) before treatment. The inoculated agar plates were then treated with the compound to be tested by spraying with a micro sprayer. The treated plates were incubated at 23.5° C. and the data was taken 24 hours after treatment. Antibacterial activities are measured by a zone of inhibited bacterial growth from the center of the agar plate and the deposit concentration in $mg/cm^2$ at the edge of the zone of inhibition ($ED_{99}$). The effectiveness of the compounds for antibacterial activity are reported in Table III in terms of the percent of the $ED_{99}$ of each compound of the $ED_{99}$ of the standard PMA (phenyl mercuric acetate).

Example B

Mycelial Inhibition

Compounds were evaluated for in vitro fungicidal effectiveness by means of a mycelial inhibition test. This test is designed to measure the fungitoxic activity of fungicidal chemicals in terms of their degree of inhibition of mycelium growth. Fungi used were *Pythium ultimum, Rhizoctonia solani, Fusarium moniloforme, Botrytis cinerea, Aspergillus niger* and *Ustilago hordeii.* Each compound to be tested was dissolved in acetone to 500 ppm concentration. Paper strips were infused with the particular mycelium growth by covering the paper with a potato dextrose broth culture of mycelial suspension. The papers were then placed on potato dextrose agar plates and sprayed by means of a micro sprayer with the fungicidal solution. The treated paper strips were incubated at 25° C. and the data is taken after 24 hours. Fungicial activities are measured by a zone of inhibited mycelial growth from the center of the paper strips in terms of $mg/cm^2$ needed for 99% control of the fungus ($ED_{99}$). The effectiveness of the compounds for fungicidal activity are reported in Table IV in terms of the percent of the $ED_{99}$ of the test compound of the $ED_{99}$ of the standard Difolatan®.

Example C

Tomato Late Blight

Compounds were tested for the preventative control of the Tomato Late Blight organism *Phytophthora infestans*. Five- to six-week-old tomato (cultivar Bonny Best) seedlings were used. The tomato plants were sprayed with a 200-ppm suspension of the test compound in acetone, water and a nonionic emulsifier. The sprayed plants were then inoculated 1 day later with the organism, placed in an environmental chamber and incubated at 66° F. to 68° F. and 100% relative humidity for at least 16 hours. Following the incubation, the plants were maintained in a greenhouse for approximately 7 days. The percent disease control provided by a given test compound was based on the percent disease reduction relative to untreated check plants. The results are tabulated in Table V.

Example D

Rice Blast

Compounds of this invention were tested for control of the Rice Blast organism *Piricularia oryzae*, using 10- to 14-day-old rice plant seedlings (Calrose M-9 variety). Seedling plants were sprayed with a 625-ppm solution of the test compound in acetone, water and a nonionic emulsifier (ORTHO X-77 spreader). The sprayed plants were inoculated 1 day later with the organism in an environmental chamber. After inoculation, the plants were kept in an environmental chamber for about 48 hours under conditions of about 72° F. to 75° F. and about 100% relative humidity. Following the incubation period, the plants were placed in a greenhouse with a temperature of about 72° F. and maintained with bottom watering for about 12 to 16 days. The percent disease control provided by a given test compound is based on a comparison of the percentage disease relative to the percent disease development on the untreated check plants:

$$\% \text{ Control} = 100 - 100 \times \left( \frac{\% \text{ disease in treated plants}}{\% \text{ disease in check}} \right)$$

The results are tabulated in Table V.

Example G

Tomato Early Blight

Compounds were tested for the control of the Tomato Early Blight organism *Alternaria solani conidia*. Tomato (variety Bonny Best) seedlings of 6- to 7-weeks old were used. The tomato plants were sprayed with a 200-ppm solution of the test compound in an acetone-and-water solution containing a small amount of a nonionic emulsifier. The sprayed plants were inoculated 1 day later with the organism, placed in the environmental chamber and incubated at 66° F. to 68° F. and 100% relative humidity for 24 hours. Following the incubation, the plants were maintained in a greenhouse for about 12 days. Percent disease control was based on the percent disease development on untreated check plants. The results are tabulated in Table V.

Example F

Celery Late Blight

The Celery Late Blight tests were conducted using celery (Utah) plants 11 weeks old. The Celery Late Blight organism was *Septoria apii*. The celery plants were sprayed with 200-ppm solutions of the candidate toxicant mixed with acetone, water and a nonionic emulsifier. The plants were then inoculated with the organism and placed in an environmental chamber and incubated at 66° F. to 68° F. in 100% relative humidity for an extended period of time (approximately 48 hours). Following the incubation, the plants were allowed to dry and then were maintained in a greenhouse for approximately 14 days. The percent disease control provided by a given test compound is based on the percent disease reduction relative to untreated check plants. The results are reported in Table V.

Example G

Bean Powdery Mildew

Compounds were tested for the control of the Bean Powdery Mildew organism *Erysiphe polygoni*. Seedling bean plants were sprayed with a 250-ppm solution of the test compound in acetone, water and a nonionic emulsifier. The sprayed plants were then inoculated 1 day later with the organism. The plants were maintained for 10 days at temperatures of 68° F. at night with daytime temperatures of 72° F. to 80° F.; relative humidity was maintained at 40% to 60%. The percent disease control provided by a given test compound was based on the percent disease reduction relative to the untreated check plants. The results as percent control are tabulated in Table V.

Example H

Bean Rust

Compounds were evaluated for their ability to eradicate Bean Rust caused by *Uromyces phaseoli typica* on pinto beans.

Pinto bean plants, variety Idaho 1-11, 16 (summer) or 19 (winter) days old were inoculated with a 50-ppm suspension of urediospores in water containing a small amount of nonionic surfactant. The inoculated plants were placed in an environmental chamber immediately after inoculation and incubated 20 hours. Following the incubation period, the plants were removed from the chamber and placed in a greenhouse maintained at 66°-68° F. and 60-80% relative humidity. Two days after inoculation, the plants were treated by spraying with a 200-ppm solution of test compound in an acetone and water carrier formulation containing a small amount of nonionic surfactant. One or two replicate pots (each containing two plants) were used for each compound. In addition one or two replicate pots were sprayed with the same carrier formulation (without a test compound) as a control (hereinafter "untreated Checks"). The plants were kept in the greenhouse until evaluated. The plants were evaluated for disease control when disease symptoms were well developed on the untreated Checks, normally about 14 days after treatment. The percentage disease control (or eradication) provided by a test compound was based on the percent disease reduction relative to the untreated Checks. The results are reported in Table V.

Example I

Mide Adult

Compounds of this invention were tested for their insecticidal activity against parathion-resistant Two-spotted Spider Mite (*Tetranychus urticae* Koch). An acetone solution of the candidate toxicant containing a small amount of nonionic emulsifier was diluted with water to 40 ppm. Lima bean leaves which were infested with mites were dipped in the toxicant solution. The results are tabulated in Table VI in terms of percent control.

Example J

Mite Egg Control

Compounds of this invention were tested for their ovicidal activity against eggs of the Two-spotted Spider Mite (*Tetranychus urticae* Koch). An acetone solution of the test toxicant containing a small amount of nonionic emulsifier was diluted with water to give a concentration of 40 ppm. Two days before testing, 2-week old lima bean plants were infested with spider mites. Two days after infestation, leaves from the infested plants are dipped in the toxicant solution, placed in a petridish with filter paper and allowed to dry in the open dish at room temperature. The treated leaves were then held in covered dishes at about 31° C. to 33° C. for seven days. On the eighth day egg mortality readings are taken. The results, expressed as percent control, are tabulated in Table VI.

TABLE I

Compounds of the Formula:

$$\begin{array}{c} R^1 \\ | \\ C-CN \\ | \\ R^2 \end{array} \quad \begin{array}{ccc} Cl & Cl \\ | & | \\ S-C-C-H \\ | & | \\ Cl & Cl \end{array}$$

$$R-S-N$$
$$\begin{array}{c} O \\ \| \\ \| \\ O \end{array}$$

| Compound | R | R¹ | R² | Physical State | %C Calc. | %C Found | %H Calc. | %H Found | %N Calc. | %N Found | %Cl Calc. | %Cl Found | %S Calc. | %S Found |
|---|---|---|---|---|---|---|---|---|---|---|---|---|---|---|
| 1 44264 | CH₃— | CH₃— | CH₃— | beige solid, mp 129–134° C. | 23.35 | 25.61 | 2.78 | 3.07 | 7.78 | 9.16 | 39.39 | 40.85 | | |
| 2 46286 | CH₃— | CH₃— | H— | white solid | 20.81 | N/A | 2.31 | N/A | 8.09 | N/A | | | | |
| 3 45569 | CH₃— | CH₃— | CH₃CH₂— | white solid, mp 121–128° C. | 25.68 | 28.68 | 3.23 | 3.67 | 7.49 | 8.08 | | | | |
| 4 45756 | CH₃— | CH₃CH₂— | CH₃CH₂— | white solid, 95–96° C. | 27.85 | 31.94 | 3.64 | 3.91 | 7.22 | 7.51 | | | | |
| 5 45863 | CH₃— | ⌬ (phenyl) | H— | brown oil | 32.35 | 32.45 | 2.45 | 2.68 | 6.86 | 6.62 | | | | |
| 6 45950 | CH₃— | ⌬ (phenyl) | CH₂— | white solid, mp 128–142° C. | 34.12 | 34.96 | 2.84 | 2.89 | 6.64 | 6.7 | | | | |
| 7 46007 | CH₃— | together form cyclopentyl | | white crystals, 143–144° C. | 27.98 | 28.01 | 3.13 | 3.36 | 7.26 | 6.70 | | | | |
| 8 45820 | CH₃— | together form cyclohexyl | | white solid, mp 97–104° C. | 33.08 | 32.38 | 3.76 | 4.09 | 3.15 | 4.13 | | | | |
| 9 46070 | CH₃— | CH₃— | thienyl | off-white solid | 28.04 | 28.43 | 2.34 | 2.51 | 6.54 | 6.62 | | | | |

TABLE I-continued
Compounds of the Formula:

$$R-S(=O)(=O)-N(-S-C(Cl)(CH Cl_2)-C(Cl)(H)Cl)-C(R^1)(R^2)-CN$$

| Compound | R | R¹ | R² | Physical State | %C Calc. | %C Found | %H Calc. | %H Found | %N Calc. | %N Found | %Cl Calc. | %Cl Found | %S Calc. | %S Found |
|---|---|---|---|---|---|---|---|---|---|---|---|---|---|---|
| 10 45622 | CH₃CH₂— | H— | H— | beige crystals, mp 65–67° C. | 20.82 | 23.14 | 2.33 | 2.65 | 8.10 | 8.56 | | | | |
| 11 45571 | CH₃CH₂— | CH₃— | CH₃— | white solid, mp 123–125° C. | 25.68 | 27.72 | 3.23 | 3.31 | 7.49 | 7.54 | | | | |
| 12 46288 | CH₃CH hd 2CH₂— | CH₃— | CH₃— | white crystals, mp 122–126° C. | 27.85 | N/A | 3.64 | N/A | 7.22 | N/A | 36.54 | N/A | 16.52 | N/A |
| 13 46072 | CH₃(CH₂)₃— | CH₃— | CH₃— | beige solid, mp 104–106° C. | 29.83 | 29.73 | 4.01 | 4.17 | 6.96 | 7.47 | | | | |
| 14 46179 | ClCH₂— | CH₃— | CH₃— | beige solid, mp 102–104° C. | 21.31 | 21.63 | 2.30 | 2.50 | 7.10 | 7.34 | | | | |
| 15 46043 | ClCH₂CH₂CH₂— | CH₃— | CH₃— | brown solid, mp 68–71° C. | 25.58 | 25.85 | 3.10 | 3.2 | 6.63 | 7.09 | 41.85 | 43.5 | 15.17 | 15.0 |
| 16 46029 | CH₂=CH— | CH₃— | CH₃— | beige solid, mp 130–131° C. | 25.81 | 26.24 | 2.71 | 2.89 | 7.52 | 8.61 | | | | |
| 17 44312 | (phenyl) | H— | H— | beige solid, mp 106–108° C. | 30.48 | 32.14 | 2.03 | 2.28 | 7.11 | 7.72 | | | | |
| 18 44040 | (2-nitrophenyl) | H— | H— | off-white solid, mp 127–130° C. | 27.35 | 29.03 | 1.60 | 1.66 | 9.57 | 10.5 | | | | |
| 19 43875 | (4-nitrophenyl) | H— | H— | yellow solid, mp 140–142° C. | 27.35 | 29.27 | 1.59 | 1.91 | 9.57 | 10.03 | | | | |

TABLE I-continued

Compounds of the Formula:

$$\begin{array}{c} R^1 \\ | \\ C-CN \\ | \\ R^2 \\ | \\ O \quad N-S-C-C-H \\ \| \quad | \quad | \quad | \\ R-S \quad Cl \quad Cl \quad Cl \\ \| \\ O \end{array}$$

| Compound | R | R¹ | R² | Physical State | %C Calc. | %C Found | %H Calc. | %H Found | %N Calc. | %N Found | %Cl Calc. | %Cl Found | %S Calc. | %S Found |
|---|---|---|---|---|---|---|---|---|---|---|---|---|---|---|
| 20 46295 | (3-CF₃-C₆H₄-CH₂-) | CH₃— | CH₃— | beige solid, mp 128–130° C. | 33.28 | 34.45 | 2.57 | 2.74 | 5.54 | 6.43 | | | | |
| 21 45979 | CH₃OCH₂CH₂— | CH₃— | CH₃— | beige solid, mp 83–85° C. | 26.75 | 29.41 | 3.49 | 4.55 | 6.93 | 7.7 | | | | |
| 22 46093 | CH₃CH₂OCH₂CH₂— | CH₃— | CH₃— | beige solid, mp 69–70° C. | 28.73 | 27.72 | 3.86 | 4.46 | 6.70 | 6.46 | | | | |
| 23 45895 | CH₃OCCH₂CH₃ (O=) | CH₃— | CH₃— | light brown solid, mp 133–135° C. | 27.79 | 28.07 | 3.27 | 3.51 | 6.48 | 6.56 | | | | |
| 24 45891 | CH₃CH₂OCCH₂CH₂— (O=) | CH₃— | CH₃— | beige solid, mp 85–87° C. | 27.65 | 29.07 | 3.71 | 3.77 | 6.45 | 6.32 | | | | |
| 25 46119 | CH₃SCH₂CH₂— | CH₃— | CH₃— | white crystals, mp 84° C. | 25.72 | 25.86 | 3.36 | 3.64 | 6.66 | 7.24 | 33.75 | 34.2 | 22.89 | 23.2 |
| 26 46230 | CH₃SCH₂CH₂— (O=) | CH₃— | CH₃— | white crystals, mp 119–120° C. | 24.78 | 24.76 | 3.23 | 3.39 | 6.42 | 6.59 | 32.51 | 32.0 | 22.05 | 21.15 |
| 27 45819 | CH₃SO₂CH₂CH₂— | CH₃— | CH₃— | white crystals, mp 120–123° C. | 23.90 | 23.92 | 3.12 | 3.26 | 6.20 | 7.02 | 31.36 | 31.9 | 21.27 | 22.4 |

N/A = Not available

TABLE II

Compounds of the Formula:

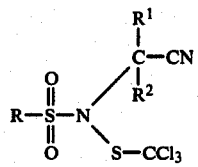

| Compound | R | R¹ | R² | Physical State | %C Calc. | %C Found | %H Calc. | %H Found | %N Calc. | %N Found |
|---|---|---|---|---|---|---|---|---|---|---|
| 28 44263 | $CH_3-$ | $CH_3-$ | $CH_3-$ | beige solid, mp 99–103° C. | 23.13 | 24.57 | 2.89 | 3.12 | 8.99 | 9.93 |
| 29 45570 | $CH_3-$ | $CH_3CH_2-$ | $CH_3-$ | white solid, mp 61–63° C. | 25.81 | 28.34 | 3.40 | 3.72 | 8.60 | 8.80 |
| 30 45794 | $CH_3-$ | $CH_3CH_2-$ | $CH_3CH_2-$ | white solid, mp 67–69° C. | 28.28 | 28.54 | 3.86 | 3.90 | 8.25 | 8.39 |
| 31 45926 | $CH_3-$ | together form | (cyclopentyl) | white solid, mp 114–116° C. | 28.45 | 27.65 | 3.28 | 3.41 | 8.30 | 8.71 |
| 32 45623 | $CH_3CH_2-$ | H— | H— | white crystals, mp 73–74° C. | 20.18 | 23.69 | 2.37 | 2.67 | 9.42 | 9.78 |
| 33 45706 | $CH_3CH_2-$ | $CH_3-$ | $CH_3-$ | beige crystals, mp 72–74° C. | 25.81 | 28.68 | 3.41 | 3.65 | 8.60 | 9.12 |
| 34 46299 | $ClCH_2-$ | $CH_3-$ | $CH_3-$ | white solid, mp 78–80° C. | 20.82 | 20.58 | 2.33 | 2.35 | 8.09 | 8.40 |
| 35 46028 | $CH_2=CH-$ | $CH_3-$ | $CH_3-$ | yellow oil | 25.98 | 25.6 | 2.80 | 3.29 | 8.66 | 8.89 |
| 36 44311 | phenyl | H— | H— | beige solid, mp 61–62° C. | 31.28 | 32.78 | 2.02 | 2.13 | 8.10 | 8.78 |
| 37 44217 | 4-$CH_3$-phenyl | H— | H— | white solid, mp 127–129° C. | 33.40 | 34.22 | 2.50 | 2.58 | 7.79 | 8.48 |
| 38 44110 | 4-Cl-phenyl | H— | H— | white solid, mp 163–165° C. | 28.44 | 29.17 | 1.58 | 1.56 | 7.37 | 6.93 |
| 39 43958 | 2-$NO_2$-phenyl | H— | H— | beige solid, mp 87–94° C. | 27.67 | 28.27 | 1.54 | 1.83 | 10.70 | 11.24 |
| 40 43874 | 4-$NO_2$-phenyl | H— | H— | yellow solid, mp 125–127° C. | 27.67 | 28.87 | 1.53 | 1.58 | 10.76 | 11.47 |
| 41 44216 | phenyl-$CH_2-$ | H— | H— | beige solid, mp 116–117° C. | 33.40 | 34.4 | 2.50 | 2.82 | 7.79 | 8.22 |

TABLE II-continued

Compounds of the Formula:

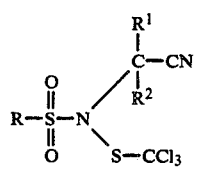

| Compound | R | R¹ | R² | Physical State | %C Calc. | %C Found | %H Calc. | %H Found | %N Calc. | %N Found |
|---|---|---|---|---|---|---|---|---|---|---|
| 42 46375 | CF₃—(phenyl)—CH₂— | H— | H— | yellow oil-solid | 30.89 | 30.9 | 1.89 | 2.08 | 6.55 | 6.59 |
| 43 45977 | CH₃OCH₂CH₂— | CH₃— | CH₃— | yellow semi-solid | 27.0 | 26.91 | 3.68 | 4.49 | 7.88 | 7.92 |
| 44 46094 | CH₃CH₂OCH₂CH₂— | CH₃— | CH₃— | beige solid, mp 63–64° C. | 29.25 | 30.91 | 4.09 | 5.56 | 7.58 | 7.74 |
| 45 45896 | CH₃OC(O)CH₂— | CH₃— | CH₃— | light brown solid, mp 87–88° C. | 28.17 | 28.41 | 3.42 | 4.01 | 7.30 | 8.13 |
| 46 45892 | CH₃CH₂OC(O)CH₂CH₂— | CH₃— | CH₃— | amber oil | 30.19 | 29.22 | 3.80 | 3.97 | 7.40 | 7.14 |

TABLE III

Bacterial Inhibition

| Compound | Pseudo | Erwin. | Xanth. |
|---|---|---|---|
| 1 44264 | 0 | 44 | 100 |
| 2 46286 | 100 | 38 | 100 |
| 3 45569 | 100 | 26 | 100 |
| 4 45756 | 0 | 0 | 0 |
| 5 45863 | 19 | 0 | 100 |
| 6 45950 | 50 | 0 | 75 |
| 7 46007 | 94 | 0 | 100 |
| 8 45820 | 0 | 0 | 25 |
| 9 46070 | 75 | 50 | 88 |
| 10 45622 | 50 | 100 | 100 |
| 11 45571 | 100 | 21 | 100 |
| 12 45288 | 0 | 0 | 100 |
| 13 46072 | 38 | 0 | 0 |
| 14 46179 | 27 | 0 | 100 |
| 15 46043 | 88 | 38 | 100 |
| 16 46029 | 43 | 0 | 100 |
| 17 44312 | 36 | 0 | 100 |
| 18 44040 | 0 | 0 | 48 |
| 19 43875 | 19 | 0 | 78 |
| 20 46295 | 30 | 0 | 0 |
| 21 45979 | 85 | 0 | 100 |
| 22 46093 | 62 | 0 | 0 |
| 23 45895 | 69 | 0 | 64 |
| 24 45891 | 50 | 0 | 50 |
| 25 46119 | 56 | 0 | 0 |
| 26 46230 | 22 | 0 | 61 |
| 27 45819 | 28 | 0 | 50 |
| 28 44263 | 0 | 0 | 0 |
| 29 45570 | 0 | 0 | 19 |
| 30 45794 | 0 | 0 | 100 |
| 31 45936 | 0 | 0 | 63 |
| 32 45623 | 34 | 63 | 43 |
| 33 45706 | 0 | 0 | 0 |
| 34 46299 | 0 | 0 | 33 |
| 35 46028 | 0 | 0 | 50 |
| 36 44311 | 0 | 0 | 100 |
| 37 44217 | 0 | 0 | 0 |
| 38 44110 | 28 | 0 | 0 |
| 39 43958 | 0 | 0 | 0 |
| 40 43874 | 0 | 0 | 0 |
| 41 44216 | 0 | 0 | 0 |
| 42 46375 | 0 | 0 | 22 |
| 43 45977 | 0 | 0 | 0 |
| 44 46094 | 0 | 0 | 0 |
| 45 45896 | 0 | 0 | 0 |
| 46 45892 | 0 | 0 | 0 |

Pseudo = *Pseudomonas syringae*
Erwin. = *Erwinia amylovora*
Xanth. = *Xanthomonas vesicatoria*

TABLE IV

Mycelial Inhibition

| Compound | Pyth. | Rhiz. | Fusar. | Botry. | Asper. | Ustil. |
|---|---|---|---|---|---|---|
| 1 44264 | 63 | 160 | 71 | 100 | 71 | 229 |
| 2 46286 | 100 | 100 | 55 | 100 | 167 | 100 |
| 3 45569 | 42 | 100 | 120 | 100 | 51 | 97 |
| 4 45756 | 32 | 100 | 59 | 69 | 94 | 58 |
| 5 45863 | 0 | 0 | 0 | 33 | 0 | 16 |
| 6 45950 | 21 | 33 | 91 | 100 | 0 | 67 |
| 7 46007 | 34 | 94 | 43 | 100 | 0 | 46 |
| 8 45820 | 0 | 63 | 0 | 26 | 0 | 43 |
| 9 46070 | 38 | 100 | 88 | 100 | 42 | 69 |
| 10 45622 | 100 | 100 | 68 | 100 | 87 | 200 |
| 11 45571 | 38 | 100 | 120 | 100 | 89 | 92 |
| 12 46288 | 21 | 57 | 35 | 100 | 0 | 88 |
| 13 46072 | 50 | 100 | 52 | 100 | 0 | 60 |
| 14 46179 | 0 | 28 | 49 | 100 | 52 | 100 |
| 15 46043 | 26 | 114 | 71 | 100 | 49 | 50 |
| 16 46029 | 0 | 114 | 58 | 38 | 79 | 72 |
| 17 44312 | 24 | 104 | 0 | 73 | 0 | 117 |
| 18 44040 | 0 | 64 | 0 | 54 | 0 | 114 |
| 19 43875 | 73 | 100 | 60 | 56 | 0 | 70 |
| 20 46295 | 0 | 17 | 0 | 26 | 0 | 0 |
| 21 45979 | 41 | 69 | 35 | 85 | 130 | 0 |
| 22 46093 | 38 | 100 | 73 | 100 | 23 | 62 |

TABLE IV-continued

Mycelial Inhibition

| Compound | Pyth. | Rhiz. | Fusar. | Botry. | Asper. | Ustil. |
|---|---|---|---|---|---|---|
| 23 45895 | 88 | 81 | 78 | 100 | 91 | 100 |
| 24 45891 | 75 | 56 | 83 | 65 | 66 | 100 |
| 25 46119 | 22 | 100 | 61 | 100 | 0 | 71 |
| 26 46230 | 23 | 26 | 0 | 61 | 0 | 22 |
| 27 45819 | 29 | 58 | 0 | 19 | 0 | 25 |
| 28 44263 | 0 | 30 | 0 | 0 | 0 | 0 |
| 29 45570 | 0 | 0 | 0 | 38 | 0 | 0 |
| 30 45794 | 0 | 0 | 0 | 18 | 0 | 0 |
| 31 45936 | 0 | 25 | 0 | 29 | 0 | 0 |
| 32 45623 | 43 | 38 | 0 | 50 | 0 | 53 |
| 33 45706 | 0 | 0 | 22 | 35 | 36 | 13 |
| 34 46299 | 0 | 0 | 0 | 16 | 0 | 19 |
| 35 46028 | 0 | 0 | 0 | 26 | 0 | 28 |
| 36 44311 | 14 | 66 | 0 | 0 | 0 | 45 |
| 37 44217 | 0 | 25 | 0 | 31 | 0 | 0 |
| 38 44110 | 30 | 63 | 0 | 39 | 31 | 35 |
| 39 43958 | 0 | 48 | 0 | 0 | 0 | 30 |
| 40 43874 | 100 | 88 | 0 | 60 | 0 | 35 |
| 41 44216 | 0 | 34 | 0 | 0 | 0 | 18 |
| 42 46375 | 22 | 35 | 41 | 71 | 23 | 37 |
| 43 45977 | 0 | 0 | 0 | 0 | 0 | 48 |
| 44 46094 | 0 | 20 | 0 | 0 | 0 | 0 |
| 45 45896 | 0 | 18 | 0 | 20 | 0 | 20 |
| 46 45892 | 0 | 25 | 0 | 19 | 0 | 0 |

Pyth. = *Pythium ultimum*
Rhiz. = *Rhizoctonia solani*
Fusar. = *Fusarium moniloforme*
Botry. = *Botrytis cinerea*
Asper. = *Aspergillus niger*
Ustil. = *Ustilago hordeii*

TABLE V

Fungicidal Activity

| Compound | TLB | RB | TEB | CLB | BPM | BR |
|---|---|---|---|---|---|---|
| 1 44264 | 100 | 89 | 0 | 100 | 24 | 0 |
| 2 46286 | 100 | 88 | 95 | 100 | 25 | 0 |
| 3 45569 | 97 | 0 | 89 | 95 | 0 | 0 |
| 4 45756 | 95 | — | 93 | 100 | 45 | 0 |
| 5 45863 | 33 | — | 85 | 74 | 0 | 0 |
| 6 45950 | 11 | — | 89 | 78 | 0 | 0 |
| 7 46007 | 61 | 25 | 69 | 100 | 0 | 0 |
| 8 45820 | 69 | — | 89 | 97 | 81 | 0 |
| 9 46070 | 69 | — | 94 | 87 | 21 | 0 |
| 10 45622 | 0 | 17 | 11 | 42 | 9 | 0 |
| 11 45571 | 100 | 98 | 95 | 98 | 98 | 0 |
| 12 46288 | 96 | 93 | 93 | 100 | 0 | 0 |
| 13 46072 | 90 | 95 | 100 | 97 | 64 | 0 |
| 14 46179 | 44 | 63 | 58 | 50 | 0 | 0 |
| 15 46043 | 28 | — | 74 | 100 | 0 | 0 |
| 16 46029 | 72 | — | 84 | 100 | 0 | 0 |
| 17 44312 | 95 | 100 | 0 | 97 | 98 | 0 |
| 18 44040 | 63 | 33 | 0 | 34 | 0 | 0 |
| 19 43875 | 91 | 87 | 86 | 93 | 0 | 0 |
| 20 46295 | 0 | 0 | 50 | 0 | 0 | 0 |
| 21 45979 | 83 | 81 | 47 | 100 | 36 | 0 |
| 22 46093 | 95 | 35 | 90 | 83 | 85 | 0 |
| 23 45895 | 0 | 0 | 42 | 58 | 0 | 0 |
| 24 45891 | 6 | 0 | 53 | 42 | 0 | 0 |
| 25 46119 | 50 | 0 | 90 | 93 | 0 | 0 |
| 26 46230 | 63 | 50 | 0 | 67 | 0 | 0 |
| 27 45819 | 56 | — | 63 | 93 | 25 | 0 |
| 28 44263 | 0 | 0 | 0 | 0 | 0 | 0 |
| 29 45570 | 0 | 0 | 14 | 92 | 0 | 0 |
| 30 45794 | 0 | — | 25 | 75 | 0 | 0 |
| 31 45936 | 0 | 50 | 0 | 0 | 0 | 0 |
| 32 45623 | 0 | 0 | 0 | 0 | 0 | 0 |
| 33 45706 | 56 | 0 | 10 | 0 | 80 | 0 |
| 34 46299 | 0 | 0 | 0 | 0 | 0 | 0 |
| 35 46028 | 0 | — | 67 | 0 | 0 | 0 |
| 36 44311 | 98 | 90 | 64 | 83 | 84 | 0 |
| 37 44217 | 88 | 78 | 63 | 81 | 96 | 0 |
| 38 44110 | 0 | 86 | 83 | 67 | 45 | 0 |
| 39 43958 | 81 | 83 | 57 | 75 | 87 | 0 |
| 40 43874 | 99 | 42 | 64 | 86 | 86 | 0 |
| 41 44216 | 91 | 67 | 50 | 81 | 80 | 0 |
| 42 46375 | 69 | 0 | 82 | 94 | 100 | 0 |
| 43 45977 | 0 | 0 | 0 | 0 | 0 | 0 |
| 44 46094 | 13 | 0 | 57 | 0 | 0 | 0 |
| 45 45896 | 0 | 0 | 58 | 92 | 29 | 0 |
| 46 45892 | 0 | 50 | 17 | 17 | 43 | 0 |

TLB = Tomato Late Blight
RB = Rice Blast
TEB = Tomato Early Blight
CLB = Celery Late Blight
BPM = Bean Powdery Mildew
BR = Bean Rust
— = Not tested or test failed

TABLE VI

Miticidal Activity

| Compound | MA | ME |
|---|---|---|
| 1 44264 | 0 | 100 |
| 2 46286 | 0 | 0 |
| 3 45569 | 0 | 100 |
| 4 45756 | 95 | 100 |
| 5 46863 | 0 | 0 |
| 6 45950 | 0 | 90 |
| 7 46007 | 0 | 86 |
| 8 45820 | 0 | 90 |
| 9 46070 | 30 | 0 |
| 10 45622 | 0 | 0 |
| 11 45571 | 60 | 100 |
| 12 46288 | 0 | 90 |
| 13 46072 | 0 | 100 |
| 14 46179 | 30 | 100 |
| 15 46043 | 0 | 100 |
| 16 46029 | 0 | 60 |
| 17 44312 | 0 | 100 |
| 18 44040 | 0 | 30 |
| 19 43875 | 0 | 50 |
| 20 46295 | 0 | 0 |
| 21 45979 | 0 | 100 |
| 22 46093 | 0 | 90 |
| 23 45895 | 0 | 0 |
| 24 45891 | 0 | 100 |
| 25 46119 | 0 | 0 |
| 26 46230 | 0 | 0 |
| 27 45819 | 0 | 50 |
| 28 44263 | 0 | 0 |
| 29 45570 | 0 | 0 |
| 30 45794 | 0 | 0 |
| 31 45936 | 0 | 30 |
| 32 45623 | 0 | 0 |
| 33 45706 | 0 | 0 |
| 34 46299 | 0 | 0 |
| 35 46028 | 0 | 0 |
| 36 44311 | 0 | 30 |
| 37 44217 | 0 | 0 |
| 38 44110 | 0 | 0 |
| 39 43958 | 0 | 0 |
| 40 43874 | 0 | 0 |
| 41 44216 | 0 | 0 |
| 42 46375 | 0 | 0 |
| 43 45977 | — | 0 |
| 44 46094 | 0 | 0 |
| 45 45896 | 0 | 0 |
| 46 45892 | 0 | 0 |

— = Not tested or test failed

What is claimed is:
1. A compound of the formula:

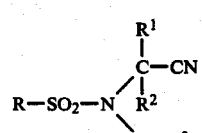

wherein R is aryl of 6 to 12 carbon atoms or aralkyl of 7 to 14 carbon atoms, either optionally substituted with 1 to 3 substituents independently selected from lower alkyl of 1 to 6 carbon atoms, lower alkoxy of 1 to 6 carbon atoms, cycloalkyl of 3 to 10 carbon atoms, lower alkylthio of 1 to 6 carbon atoms, lower alkylsulfinyl of 1 to 6 carbon atoms, lower alkylsulfonyl of 1 to 6 carbon atoms, halogen, trihalomethyl, nitro, cyano or carboxyl; alkyl of 1 to 10 carbon atoms, lower alkenyl of 2 to 6 carbon atoms, or lower alkynyl of 2 to 6 carbon atoms, all optionally substituted with 1 to 3 halogen atoms; lower alkoxyalkylene; lower alkylene carbalkoxy; lower alkylthioalkylene; lower alkylsulfinylalkylene; or lower alkylsulfonylalkylene; $R^1$ and $R^2$ are independently hydrogen, lower alkyl of 1 to 6 carbon atoms, aryl or thienyl, or taken together form an alkylene bridge to give a cycloalkyl group of 3 to 10 carbon atoms; and $R^3$ is alkyl of 1 to 3 carbon atoms substituted with 3 to 6 halogen atoms or trihalovinyl.

2. A compound according to claim 1 wherein R is lower alkyl or lower alkenyl.

3. A compound according to claim 2 wherein at least one of $R^1$ and $R^2$ is lower alkyl or $R^1$ and $R^2$ taken together form a cycloalkyl group.

4. A compound according to claim 3 wherein $R^3$ is 1,1,2,2-tetrachloroethyl.

5. A compound according to claim 4 wherein $R^2$ is thienyl.

6. A compound according to claim 4 wherein $R^1$ and $R^2$ form a cycloalkyl group.

7. A compound according to claim 6 wherein R is methyl.

8. A compound according to claim 7 wherein $R^1$ and $R^2$ form a cyclopentyl group.

9. A compound according to claim 7 wherein $R^1$ and $R^2$ form a cyclohexyl group.

10. A compound according to claim 1 wherein R is lower alkoxyalkylene.

11. A compound according to claim 10 wherein $R^1$ and $R^2$ are independently hydrogen or lower alkyl.

12. A compound according to claim 11 wherein $R^3$ is 1,1,2,2-tetrachloroethyl.

13. A compound according to claim 1 wherein R is lower alkylene carbalkoxy.

14. A compound according to claim 1 wherein $R^1$ and $R^2$ are independently hydrogen or lower alkyl.

15. A compound according to claim 14 wherein $R^3$ is 1,1,2,2-tetrachloroethyl.

16. A compound according to claim 1 wherein R is lower alkylthioalkylene, lower alkylsulfinylalkylene or lower alkylsulfonylalkylene.

17. A compound according to claim 16 wherein $R^1$ and $R^2$ are independently hydrogen or lower alkyl.

18. A compound according to claim 17 wherein $R^3$ is 1,1,2,2-tetrachloroethyl.

19. A compound according to claim 1 wherein one of $R^1$ and $R^2$ is phenyl or thienyl.

20. A compound according to claim 19 wherein R is lower alkyl.

21. A compound according to claim 20 wherein $R^3$ is 1,1,2,2-tetrachloroethyl.

22. A compound according to claim 1 wherein $R^3$ is 1,1,2,2-tetrachloroethyl.

23. A compound of the formula:

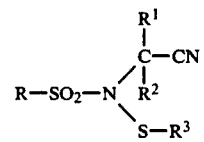

wherein R is aryl of 6 to 12 carbon atoms or aralkyl of 7 to 14 carbon atoms, either optionally substituted with 1 to 3 substituents independently selected from lower alkyl of 1 to 6 carbon atoms, lower alkoxy of 1 to 6 carbon atoms, cycloalkyl of 3 to 10 carbon atoms, lower alkylthio of 1 to 6 carbon atoms, halogen, nitro, cyano or carboxyl; or alkyl of 1 to 10 carbon atoms, lower alkenyl of 2 to 6 carbon atoms, or lower alkynyl of 2 to 6 carbon atoms, all optionally substituted with 1 to 3 halogen atoms; $R^1$ is hydrogen, or lower alkyl of 1 to 6 carbon atoms; $R^2$ is hydrogen, or lower alkyl of 1 to 6 carbon atoms; and $R^3$ is alkyl of 1 to 3 carbon atoms substituted with 3 to 6 halogen atoms or trihalovinyl.

24. A compound according to claim 23 wherein R is lower alkyl.

25. A compound according to claim 24 wherein $R^3$ is 1,1,2,2-tetrachloroethyl.

26. A compound according to claim 25 wherein $R^1$ and $R^2$ are independently lower alkyl.

27. A compound according to claim 26 wherein R, $R^1$ and $R^2$ are methyl.

28. A compound according to claim 23 wherein R is phenyl or substituted phenyl.

29. A compound according to claim 28 wherein $R^1$ and $R^2$ are hydrogen.

30. A compound according to claim 29 wherein R is phenyl.

31. A compound according to claim 30 wherein $R^3$ is 1,1,2,2-tetrachloroethyl.

32. A compound according to claim 30 wherein $R^3$ is trichloromethyl.

33. A compound according to claim 29 wherein R is 4-nitrophenyl.

34. A compound according to claim 33 wherein $R^3$ is 1,1,2,2-tetrachloroethyl.

35. A compound according to claim 33 wherein $R^3$ is trichloromethyl.

36. A compound according to claim 23 wherein $R^3$ is tetrachloroethyl, trichloromethyl, trichlorovinyl, dichlorofluoromethyl, or 2-fluoro-1,1,2,2-tetrachloroethyl.

37. A compound according to claim 23 wherein $R^3$ is 1,1,2,2-tetrachloroethyl.

38. A compound according to claim 37 wherein R is lower alkyl.

39. A compound according to claim 23 wherein $R^3$ is trichloromethyl.

40. A compound according to claim 39 wherein R is aryl, substituted aryl, aralkyl or substituted aralkyl.

41. A compound according to claim 23 wherein R is methyl, $R^1$ is methyl, $R^2$ is ethyl and $R^3$ is 1,1,2,2-tetrachloroethyl.

42. A compound according to claim 23 wherein R is n-butyl, $R^1$ is methyl, $R^2$ is methyl and $R^3$ is 1,1,2,2-tetrachloroethyl.

43. A compound according to claim 23 wherein R is vinyl, $R^1$ is methyl, $R^2$ is methyl and $R^3$ is 1,1,2,2-tetrachloroethyl.

44. A compound according to claim 23 wherein R is ethyl, $R^1$ is methyl, $R^2$ is methyl and $R^3$ is 1,1,2,2-tetrachloroethyl.

45. A compound according to claim 23 wherein R is methyl, $R^1$ is methyl, $R^2$ is hydrogen and $R^3$ is 1,1,2,2-tetrachloroethyl.

46. A method of controlling fungi which comprises contacting said fungi or their growth environment with a fungicidally effective amount of a compound of claim 1.

47. A method of controlling fungi which comprises contacting said fungi or their growth environment with a fungicidally effective amount of a compound of claim 4.

48. A method of controlling fungi which comprises contacting said fungi or their growth environment with a fungicidally effective amount of a compound of claim 8.

49. A method of controlling fungi which comprises contacting said fungi or their growth environment with a fungicidally effective amount of a compound of claim 9.

50. A method of controlling fungi which comprises contacting said fungi or their growth environment with a fungicidally effective amount of a compound of claim 12.

51. A method of controlling fungi which comprises contacting said fungi or their growth environment with a fungicidally effective amount of a compound of claim 15.

52. A method of controlling fungi which comprises contacting said fungi or their growth environment with a fungicidally effective amount of a compound of claim 18.

53. A method of controlling fungi which comprises contacting said fungi or their growth environment with a fungicidally effective amount of a compound of claim 21.

54. A method of controlling fungi which comprises contacting said fungi or their growth environment with a fungicidally effective amount of a compound of claim 22.

55. A method of controlling fungi which comprises contacting said fungi or their growth environment with a fungicidally effective amount of a compound of claim 23.

56. A method of controlling fungi which comprises contacting said fungi or their growth environment with a fungicidally effective amount of a compound of claim 27.

57. A method of controlling fungi which comprises contacting said fungi or their growth environment with a fungicidally effective amount of a compound of claim 31.

58. A method of controlling fungi which comprises contacting said fungi or their growth environment with a fungicidally effective amount of a compound of claim 32.

59. A method of controlling fungi which comprises contacting said fungi or their growth environment with a fungicidally effective amount of a compound of claim 34.

60. A method of controlling fungi which comprises contacting said fungi or their growth environment with a fungicidally effective amount of a compound of claim 35.

61. A method of controlling fungi which comprises contacting said fungi or their growth environment with a fungicidally effective amount of a compound of claim 41.

62. A method of controlling fungi which comprises contacting said fungi or their growth environment with a fungicidally effective amount of a compound of claim 42.

63. A method of controlling fungi which comprises contacting said fungi or their growth environment with a fungicidally effective amount of a compound of claim 43.

64. A method of controlling fungi which comprises contacting said fungi or their growth environment with a fungicidally effective amount of a compound of claim 44.

65. A method of controlling fungi which comprises contacting said fungi or their growth environment with a fungicidally effective amount of a compound of claim 45.

66. A fungicidal composition which comprises an inert carrier and a fungicidally effective amount of a compound of claim 1.

67. A fungicidal composition which comprises an inert carrier and a fungicidally effective amount of a compound of claim 4.

68. A fungicidal composition which comprises an inert carrier and a fungicidally effective amount of a compound of claim 8.

69. A fungicidal composition which comprises an inert carrier and a fungicidally effective amount of a compound of claim 9.

70. A fungicidal composition which comprises an inert carrier and a fungicidally effective amount of a compound of claim 12.

71. A fungicidal composition which comprises an inert carrier and a fungicidally effective amount of a compound of claim 15.

72. A fungicidal composition which comprises an inert carrier and a fungicidally effective amount of a compound of claim 18.

73. A fungicidal composition which comprises an inert carrier and a fungicidally effective amount of a compound of claim 21.

74. A fungicidal composition which comprises an inert carrier and a fungicidally effective amount of a compound of claim 22.

75. A fungicidal composition which comprises an inert carrier and a fungicidally effective amount of a compound of claim 23.

76. A fungicidal composition which comprises an inert carrier and a fungicidally effective amount of a compound of claim 27.

77. A fungicidal composition which comprises an inert carrier and a fungicidally effective amount of a compound of claim 31.

78. A fungicidal composition which comprises an inert carrier and a fungicidally effective amount of a compound of claim 32.

79. A fungicidal composition which comprises an inert carrier and a fungicidally effective amount of a compound of claim 34.

80. A fungicidal composition which comprises an inert carrier and a fungicidally effective amount of a compound of claim 35.

81. A fungicidal composition which comprises an inert carrier and a fungicidally effective amount of a compound of claim 41.

82. A fungicidal composition which comprises an inert carrier and a fungicidally effective amount of a compound of claim 42.

83. A fungicidal composition which comprises an inert carrier and a fungicidally effective amount of a compound of claim 43.

84. A fungicidal composition which comprises an inert carrier and a fungicidally effective amount of a compound of claim 44.

85. A fungicidal composition which comprises an inert carrier and a fungicidally effective amount of a compound of claim 45.

* * * * *

UNITED STATES PATENT AND TRADEMARK OFFICE
CERTIFICATE OF CORRECTION

PATENT NO. : 4,652,556
DATED : March 24, 1987
INVENTOR(S) : Moore et al

It is certified that error appears in the above—identified patent and that said Letters Patent are hereby corrected as shown below:

Column 43, line 47, "according to claim 1" should read --according to claim 13--.

Signed and Sealed this

Fifteenth Day of September, 1987

Attest:

DONALD J. QUIGG

*Attesting Officer*        *Commissioner of Patents and Trademarks*